US012642900B2

(12) United States Patent
Usman et al.

(10) Patent No.:  US 12,642,900 B2
(45) Date of Patent:       Jun. 2, 2026

(54) PERITONITIS SENSORS, INCLUDING PERITONITIS SENSORS FOR AUTOMATED PERITONEAL DIALYSIS SYSTEMS, AND ASSOCIATED SYSTEMS, DEVICES, AND METHODS

(71) Applicant: Byonyks Medical Devices, Inc., Itasca, IL (US)

(72) Inventors: Farrukh Usman, Chatham, NY (US); Michael Wollowitz, Chatham, NY (US); Faisal Bashir, Lahore (PK); Naveed Iftikhar, Lahore (PK)

(73) Assignee: Byonyks Medical Devices, Inc., Itasca, IL (US)

( * ) Notice: Subject to any disclaimer, the term of this patent is extended or adjusted under 35 U.S.C. 154(b) by 467 days.

(21) Appl. No.: 18/042,176

(22) PCT Filed: Aug. 20, 2021

(86) PCT No.: PCT/US2021/047017
§ 371 (c)(1),
(2) Date: Feb. 17, 2023

(87) PCT Pub. No.: WO2022/040601
PCT Pub. Date: Feb. 24, 2022

(65) Prior Publication Data
US 2024/0009363 A1      Jan. 11, 2024

Related U.S. Application Data

(60) Provisional application No. 63/068,385, filed on Aug. 21, 2020.

(51) Int. Cl.
*A61M 1/28*          (2006.01)
*A61M 1/14*          (2006.01)
(Continued)

(52) U.S. Cl.
CPC .............. *A61M 1/28* (2013.01); *A61M 1/152* (2022.05); *A61M 1/154* (2022.05); *A61M 1/155* (2022.05);
(Continued)

(58) Field of Classification Search
CPC ...... A61M 1/152; A61M 1/154; A61M 1/155; A61M 1/159; A61M 1/28; A61M 1/69;
(Continued)

(56) References Cited

U.S. PATENT DOCUMENTS 8,147,444 B2    4/2012  Alimi et al.
8,278,023 B2    10/2012  Ichikawa et al.
(Continued)

FOREIGN PATENT DOCUMENTS

CN        110 393 831 A      11/2019
EP           0178501 B1      11/1989
(Continued)

OTHER PUBLICATIONS

Written Opinion and International Search Report dated Oct. 29, 2021 for International Patent Application No. PCT/US2021/047017.
(Continued)

*Primary Examiner* — John Kim
(74) *Attorney, Agent, or Firm* — McDonnell Boehnen Hulbert & Berghoff LLP

(57)          ABSTRACT

Peritonitis sensors, including peritonitis sensors for automated peritoneal dialysis (APD) systems, and associated systems, devices, and methods are disclosed herein. In one embodiment, an APD system includes a disposable set, a portion of which is at least partially aligned with a peritonitis sensor. The peritonitis sensor can be configured to capture one or more peritonitis measurements from the solution in the disposable set. The APD system can determine whether
(Continued)

one or more peritonitis measurements indicate the presence of peritonitis in a patient from which the solution is drained. In some embodiments, if the APD system determines that one or more peritonitis measurements indicate peritonitis, the APD system can alert a user of the system to the presence of peritonitis in the patient.

20 Claims, 8 Drawing Sheets

(51) Int. Cl.
*G01N 33/487* (2006.01)
*A61M 1/00* (2006.01)

(52) U.S. Cl.
CPC ........... *A61M 1/159* (2022.05); *G01N 33/487* (2013.01); *A61M 1/69* (2021.05); *A61M 2205/18* (2013.01); *A61M 2205/3306* (2013.01)

(58) Field of Classification Search
CPC ...... A61M 2205/18; A61M 2205/3306; G01N 33/487
See application file for complete search history.

(56) References Cited

U.S. PATENT DOCUMENTS

| | | | |
|---|---|---|---|
| 8,546,097 | B2 | 10/2013 | Martis et al. |
| 8,777,891 | B2 | 7/2014 | Landherr et al. |
| 8,801,652 | B2 | 8/2014 | Landherr et al. |
| 2009/0149776 | A1 | 6/2009 | Adams |
| 2011/0186517 | A1 | 8/2011 | Hedmann et al. |
| 2017/0039700 | A1 | 2/2017 | Chen et al. |
| 2019/0228526 | A1 | 7/2019 | Wuepper et al. |
| 2019/0295256 | A1* | 9/2019 | Yang .................... G06K 7/1413 |
| 2020/0020445 | A1 | 1/2020 | Karopadi |

FOREIGN PATENT DOCUMENTS

| | | |
|---|---|---|
| WO | 2021211803 A1 | 10/2021 |
| WO | 2022027036 A1 | 2/2022 |
| WO | 2022040325 A2 | 2/2022 |
| WO | 2022040597 A1 | 2/2022 |
| WO | 2022040601 A1 | 2/2022 |
| WO | 2022051456 A1 | 3/2022 |

OTHER PUBLICATIONS

Supplementary Partial European Search Report issued on Jul. 5, 2024, in European Patent Application No. 21859248.3, 15 pages.

* cited by examiner

406

414

411

506

514

511

600

1050

1052

Align portion of disposable set with peritonitis sensor

1054

Capture one or more peritonitis measurements

1056

Measurement(s) indicate peritonitis ?

No

Yes

1058

Alert user of detection of peritonitis

PERITONITIS SENSORS, INCLUDING PERITONITIS SENSORS FOR AUTOMATED PERITONEAL DIALYSIS SYSTEMS, AND ASSOCIATED SYSTEMS, DEVICES, AND METHODS

CROSS-REFERENCE TO RELATED APPLICATION(S)

This application is a section 371 U.S. national phase of PCT/US2021/047017, filed Aug. 20, 2021, which claims the benefit of priority to U.S. Provisional Patent Application No. 63/068,385, filed Aug. 21, 2020, the entirety of both applications which is incorporated by reference herein in its entirety and for all purposes.

TECHNICAL FIELD

The present disclosure is directed to peritonitis sensors and associated systems, devices, and methods. For example, peritonitis sensors configured in accordance with some embodiments of the present technology are configured to detect indications of peritonitis in fluid flowing through a disposable set of automated peritoneal dialysis (APD) systems.

BACKGROUND

Dialysis is used to (i) remove excess fluid and toxins in persons with kidney failure and (ii) correct electrolyte concentrations in their blood. Peritoneal dialysis is a form of dialysis that uses a peritoneum in an individual's abdomen as a membrane through which fluid and dissolved substances are exchanged with blood. More specifically, a solution is introduced into and removed from the individual's abdomen via a surgically installed catheter.

In continuous ambulatory dialysis (CAPD), solution is manually introduced and removed (e.g., at regular intervals throughout the day). In particular, the catheter is connected to a disposable set that includes (i) a source bag (e.g., hung on a drip stand) containing new solution, (ii) a drain bag configured to collect waste solution, and (iii) various fluid lines connecting the source bag and the drain bag to the catheter. Waste solution from the individual's lower abdomen is drained into the drain bag via the catheter, and new solution is introduced into the individual's lower abdomen via the catheter. After such an exchange treatment is complete, the disposable set is discarded.

APD (also known as continuous cycling peritoneal dialysis (CCPD)) is similar to CAPD except that the exchange treatment is automated using an APD machine or cycler. More specifically, a pump included in the APD machine is used to introduce and remove the solution (e.g., while the individual sleeps). Each APD exchange treatment may include one or more cycles of introducing and removing solution from the individual's abdomen.

BRIEF DESCRIPTION OF THE DRAWINGS

Many aspects of the present disclosure can be better understood with reference to the following drawings. The components in the drawings are not necessarily to scale. Instead, emphasis is placed on clearly illustrating the principles of the present disclosure. The drawings should not be taken to limit the disclosure to the specific embodiments depicted, but are for explanation and understanding only.

DETAILED DESCRIPTION

Figure 1:
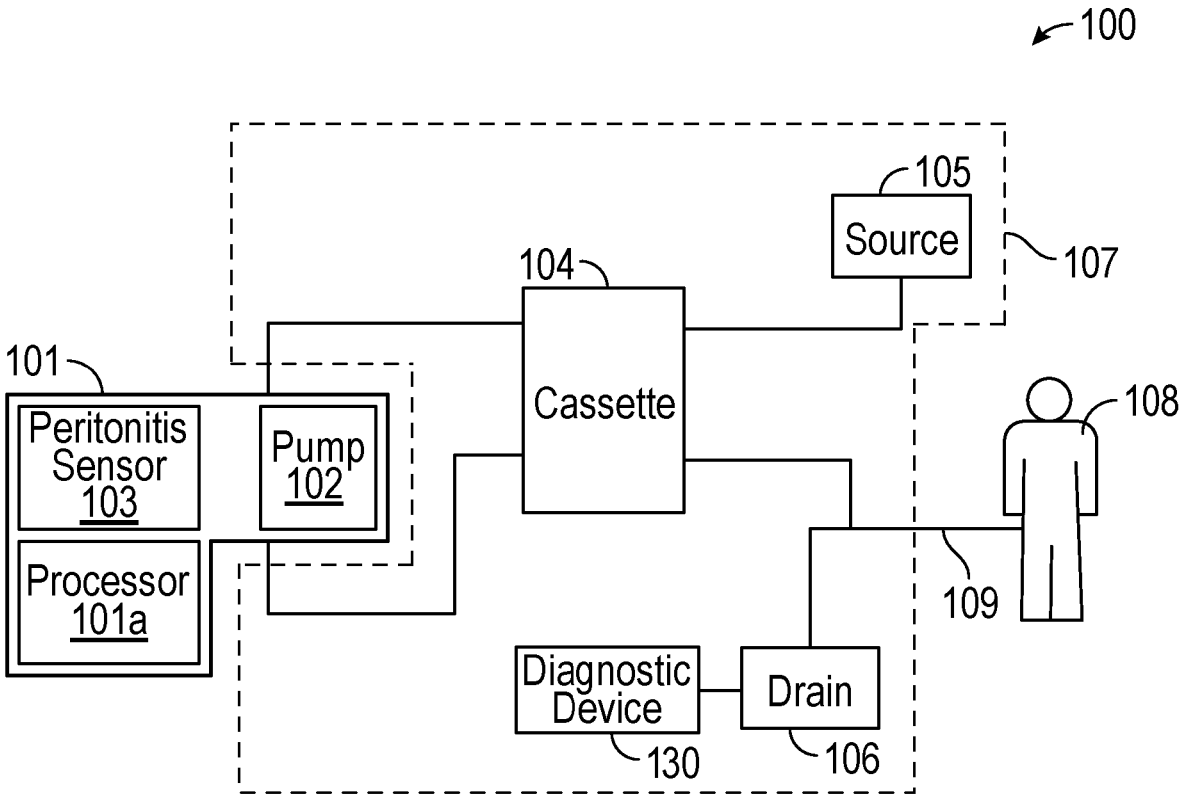
FIG. 1 is a partially schematic representation of an APD system configured in accordance with various embodiments of the present technology.

The present disclosure is directed to peritonitis sensors and associated systems, devices, and methods. In the illustrated embodiments below, peritonitis sensors of the present technology are primarily described in the context of detecting peritonitis from dialysate solution flowing through disposable sets of APD systems. Peritonitis sensors configured in accordance with various embodiments of the present technology, however, can be incorporated into and/or used b other systems, including CAPD systems, hemodialysis systems and/or other medical or non-medical systems. Additionally, peritonitis sensors of the present technology can be used to detect peritonitis from other solutions or fluids besides dialysate solution, such as water, saline, blood, and/or other low viscous fluids. Furthermore, a person skilled in the art will understand (i) that the technology may have additional embodiments than illustrated in FIGS. 1-10 and (ii) that, the technology may be practiced without several of the details of the embodiments described below with reference to FIGS. 1-10.

A. Overview

Patients receiving peritoneal dialysis treatment may contract infections, such as peritonitis, during therapy (e.g., due to contamination of equipment used during treatment). Peritonitis can cause inflammation in the peritoneum during dialysis which can lead to swelling of the peritoneum. As a result, patients that contract peritonitis typically experience symptoms such as abdominal tenderness and vomiting. In some instances, or if left undetected, peritonitis can be fatal.

In some cases, peritonitis tests are performed after the onset of symptoms in a patient. These tests can include, for example, Gram stain procedures to detect bacteria associated with peritonitis infections. There can be substantial wait-times, however, before results from these tests are received. Because many patients are diagnosed with peritonitis only after the onset of severe symptoms, delayed test results can result in potentially fatal situations where a patient's long-term wellbeing can be at risk.

Another technique for detecting peritonitis is known as the "newspaper test." Nurses and/or patients can manually perform the newspaper test by placing a newspaper underneath a patients drain bag and reading the newspaper with their naked eye(s). The dialysis solution in the drain bag is generally a clear and colorless liquid which can lose its transparency due to the presence of peritonitis and/or associated indicia. Accordingly, if the nurse or patient is unable to read the newspaper through the drain bag, this can indicate that the patient has peritonitis.

The newspaper test, however, suffers from several deficiencies. The human brain is trained to read and interpret uncertain images and misspelled texts. For example, the brain is generally able to use and understand context to make predictions. Thus, when a person is shown a blurry image or misspelled sentence, they can still generally see the image or read the sentence. For example, "You cdoul eialsy rdea thsi sentcene" because the brain can evaluate and anticipate the context of a sentence. Thus, nurses and/or patients that perform the newspaper test can fail to detect or recognize the presence of peritonitis, resulting in a false negative conclusion. Additionally, or alternatively, in some circumstances the eyesight of the nurse and/or patient can affect the outcome of the newspaper test, resulting in a false negative result or a false positive conclusion. Furthermore, in some circumstances the newspaper test relies on patients to perform the test on their own and self-report their conclusions, which can lead to patients failing to perform the test and/or failing to report the results of the test.

To address these concerns, the inventors have developed peritonitis sensing systems and associated systems, devices, and methods that are expected to safely, accurately, reliably, and affordably detect peritonitis (e.g., within a disposable set). In one embodiment, an APD system includes a disposable set, at least a portion of which is at least partially aliened with a peritonitis sensor. The peritonitis sensor cart be configured to capture one or more peritonitis measurements from a solution flowing through the disposable set. The peritonitis sensor can include optical sensors (e.g., image sensors, light-detecting sensors, etc.), chemical sensors (e.g., test strips), and/or any other suitable sensors. Based at least in part on the peritonitis measurements, the APD system can determine whether peritonitis is likely to present within a patient using the solution which is drained into the disposable set. In some embodiments, if the APD system determines that one or more peritonitis measurements indicate peritonitis is likely, present in the patient, the APD system can alert a user (e.g., the patient, a caregiver, an operator, a physician, etc.) of the system to the detection of peritonitis.

Peritonitis sensing systems configured in accordance with embodiments of the present technology can operate automatically, without or substantially without user input. In at least some embodiments, this is expected to increase the frequency of peritonitis test reporting and can alert users to the presence of peritonitis at an early stage (e.g., before the onset of severe symptoms). Additionally, at least some of the peritonitis sensing systems configured in accordance with embodiments of the present technology are expected to detect peritonitis with increased speed, sensitivity, and/or accuracy.

B. Selected Embodiments of Peritonitis Sensors, Including Peritonitis Sensors for APD Systems, and Associated Systems, Devices, and Methods FIG. 1 is a partially schematic representation of an APD system 100 ("the system 100") configured in accordance with various embodiments of the present technology. As shown, the system 100 includes a reusable component(s) 101 and a disposable set 107. The reusable component(s) 101 of FIG. 1 can include an APD machine (or cycler). In these and other embodiments, the reusable component(s) 101 can include a pump 102, a peritonitis sensor 103, and a processor 101a, In other embodiments, the pump 102, the peritonitis sensor 103, and/or the processor 101a can be disposable and/or can be a part of the disposable set 107. The disposable set 107 of FIG. 1 includes a cassette 104, a source bag 105, a drain bag 106, a peritonitis diagnostic device 130 (e.g., a test, strip), and various fluid lines extending between components of the disposable set 107 and/or the reusable component(s) 101. Other well-known components of APD systems are not illustrated in FIG. 1 or described in detail below so as to avoid unnecessarily obscuring aspects of the present technology.

In some embodiments, the pump 102 can be configured such that fluid within the disposable set is isolated from the pumping mechanism. For example, the pump 102 can be a peristaltic pump or another suitable type of pump. In these and other embodiments, the pump 102 and/or the peritonitis sensor 103 can be removably or permanently integrated into an APD machine. Alternatively, the pump 102 and/or the peritonitis sensor 103 can be components of the system 100 that are separate from an APD machine.

Various components of the disposable set 107 can interface with an APD machine. For example, a portion of the drain bag 106 can be mounted or otherwise positioned on an APD machine and/or aligned with the peritonitis sensor 103, as discussed in greater detail below. The disposable set 107 can be configured to interface (i) with the pump 102, (ii) with the peritonitis sensor 103, and/or (iii) with a catheter 109 installed in a patient 108. For example, the disposable set 107 can connect to the catheter 109 (e.g., via a transfer set (not shown)) such that the catheter 109 is placed in fluid communication with the source bag 105 and/or the drain bag 106.

In operation, the system 100 can be configured to introduce a solution (e.g., dialysate or another fluid initially contained within the source bag 105) into the patient 1108 using the pump 102 and/or via at least a first portion of the disposable set 107. The system 100 can further be configured to remove solution from the patient 108 by draining the solution (e.g., waste solution) into the drain bag 106 using the pump 102 and/or via at least a second portion of the disposable set 107. In some embodiments, a single exchange treatment can include one or more cycles of introducing solution into the patient 108 and removing solution from the patient 108. After an exchange treatment is complete, the disposable set 107 can be discarded and a separate (e.g., a new) disposable set 107 can be used for a subsequent treatment.

The peritonitis sensor 103 can be configured to capture one or more peritonitis measurements from solution flowing through at least a portion of the disposable set 107. For example, as discussed in greater detail below, the peritonitis sensor 103 can (i) be aligned with a portion of the disposable set 107 and (ii) be configured to detect or measure indicators of peritonitis that are presented in solution flowing through the portion of the disposable set 107. In some embodiments, the peritonitis sensor 103 can detect peritonitis without the peritonitis sensor 103 coming in contact with the solution (e.g., using various optical detection techniques), In other embodiments, the peritonitis sensor 103 can be configured to detect peritonitis by contacting at least a portion of the solution (e.g., using chemical reaction-based detection techniques). The portion of the disposable set 107 aligned with the peritonitis sensor 103 can include a portion or region of the drain bag 106. In these and other embodiments, the portion of the disposable set 107 aligned with the peritonitis sensor 103 can be at least a portion of a fluid line (e.g., extending between and/or in fluid communication with the catheter 109 and the drain bag 106). As discussed in greater detail below, the processor 101*a* and/or other components of the system 100 can monitor measurements captured by the peritonitis sensor 103 and/or compare the measurements to various thresholds or ranges. Using the measurements and/or the comparisons of the measurements to the thresholds of ranges, the processor 101*a* and/or other components of the system 100 can detect or predict whether the patient has peritonitis.

Figure 2:
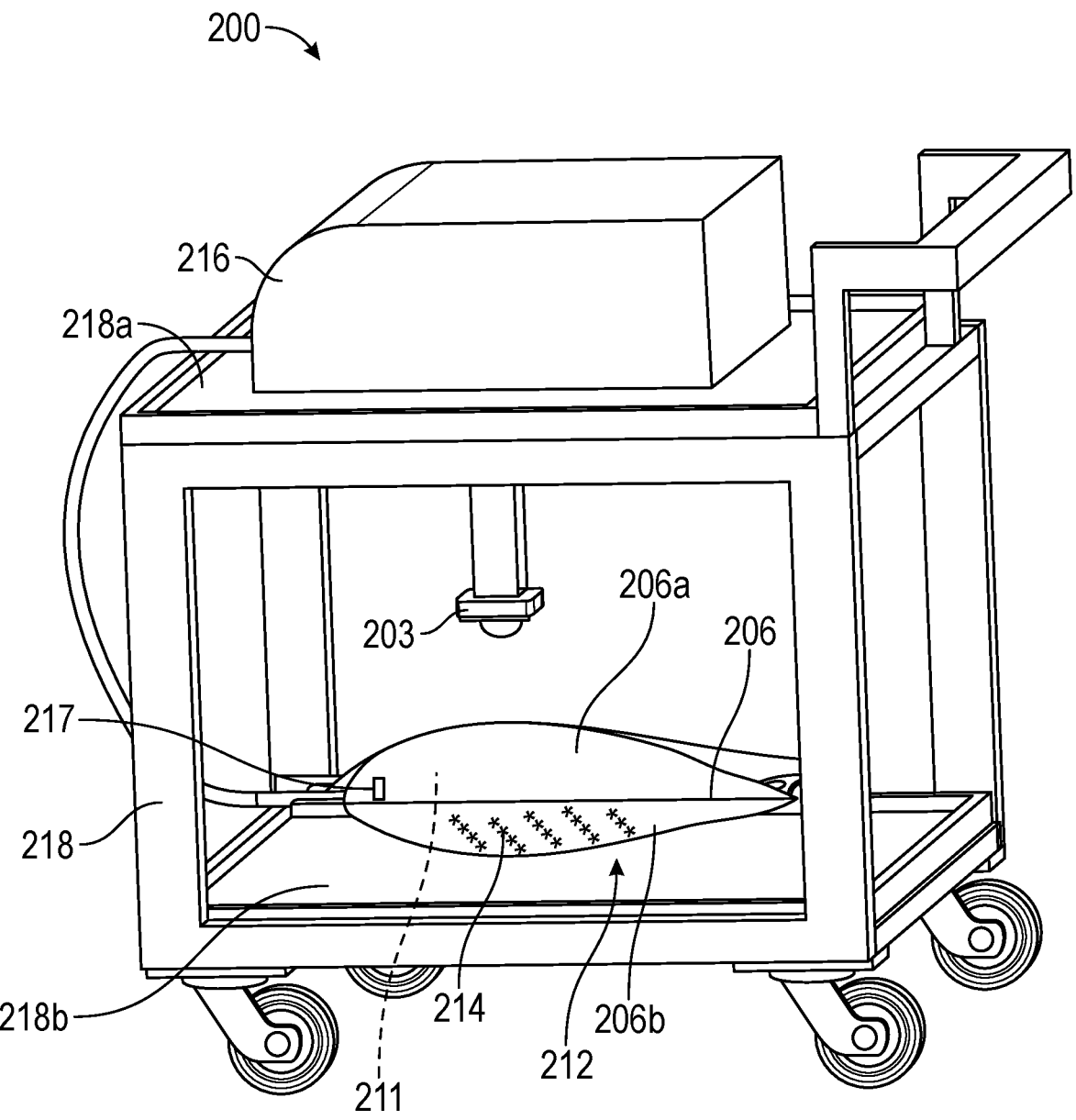
FIG. 2 is a partially schematic, perspective view of an APD system including a peritonitis sensor and a drain bag, the APD system configured in accordance with various embodiments of the present technology.

FIG. 2 is a partially schematic, perspective view of an APD system 200 ("the system 200") configured in accordance with various embodiments of the present technology. As shown, the system 200 includes a peritonitis sensor 203 and a drain bag 206. The system 200 can be at least a portion of the system 100 of FIG. 1 or at least a portion of another APD system of the present technology. Accordingly, one or more components of the system 200 (e.g., the peritonitis sensor 203, the drain bag 206, etc.) can be components of the system 100 (e.g., the peritonitis, sensor 103, the drain bag 106, etc.) or of another APD system of the present technology.

Referring first to the drain bag 206, the drain bag 206 can include a first (e.g., upper) side 206*a* or surface that, can face the peritonitis sensor 203, and a second (e.g., lower) side 206*b* opposite the first side 206*a*. The drain bag 206 is configured to receive waste solution 211 (e.g., drained from a patient's lower abdomen during an APD cycle). The second side 206*b* of the drain bag 206 includes a target region 212 having a detection feature 214. The first and/or second sides 206*a* and 206*b* are at least partially transparent, such that the detection feature 214 can be at least partially or fully visible through the first side 206*a* (e.g., from a perspective of the peritonitis sensor 203). The detection feature 214 can include text, one or more graphics, one or more images, one or more optical illusion graphic elements, one or more patterns, one or more indicia, and/or any other suitable detection feature. The detection feature 214 can be printed, embossed, or otherwise applied to an exterior surface and/or an interior surface of the second side 206*b* of the drain bag 206 using any suitable process or technique known to those of skill in the art. As described in greater detail below and with reference to FIGS. 3A-5, waste solution 211 in the drain bag 206 can at least partially reduce or otherwise change visibility of the detection feature 214, and the change in visibility can be used to detect peritonitis.

In some embodiments, the system 200 can further include an APD machine 216 configured to contain, support, or interface with one or more elements of the system 200, such as a pump (not shown in FIG. 2 for the purpose of clarity). In some embodiments, the system 200 can further include a support structure 218 configured to support one or more elements of the system 200. The support structure 218 can include a cart, a trolley, a shelf, a shelving unit, a table, and/or any other suitable support structure. The support structure 218 can include a first (e.g., upper) shelf 218*a* or surface configured to support the APD machine 216 and the peritonitis sensor 203 and a second (e.g., lower) shelf 218*b* or surface below the first shelf 218*a* and configured to support the drain bag 206. In the illustrated embodiment, for example, the peritonitis sensor 203 is mounted or fixed to an underside of the first shelf 218*a*, positioned above and at least partially aligned with the drain bag 206. In other embodiments, the drain bag 206 can be positioned above the peritonitis sensor 203, laterally from the peritonitis sensor 203, or have any other suitable position relative to the peritonitis sensor 203, in such embodiments, the relative positions and/or orientations of the first and second shelves 218*a*, 218*b* can correspond to the position and/or orientation of the drain bag 206 relative to the peritonitis sensor 203.

In some embodiments, at least a portion of the drain bag 206 can be positioned within a field of view of the peritonitis sensor 203, In the illustrated embodiment, for example, the target region 212 of the drain bag 206 is positioned within the field of view of the peritonitis sensor 203. The drain bag 206 can be positioned such that the first side 206*a* of the drain bag 206 is between the second side 206*b* of the drain bag 206 and the peritonitis sensor 203. Accordingly, the waste solution 211 in the drain bag 206 can also be positioned between the detection feature 214 and the peritonitis sensor 203, such that the peritonitis sensor 203 can visualize or otherwise attempt to observe the detection feature 214 through the waste solution 211. Thus, the relative transparency or opacity of the waste solution 211 in the drain bag 206 can affect the ability (e.g., of a user, a clinician, the peritonitis sensor 203, etc.) to visualize the detection feature 214 through the waste solution 211.

The peritonitis sensor 203 can be configured to obtain (e.g., capture) one or more peritonitis readings or measurements from the waste solution 211 and/or the drain bag 206 (e.g., to detect peritonitis). In the illustrated embodiment, for example, the peritonitis sensor 203 includes an imaging component operable to obtain one or more images of the detection feature 214 through the first side 206*a*, the waste solution 211, and/or the second side 206*b* of the drain bag 206. For example, the peritonitis sensor 203 can include an arrangement of one or more lenses and/or optical image sensors (e.g., one or more digital cameras) directed towards the drain bag 206. In some embodiments, the peritonitis sensor 203 may also include one or more light sources configured to illuminate features on the drain bag 206. In some embodiments, the system 200 (e.g., a processor or controller (not shown) of and/or operably associated with the system 200) can perform optical character recognition (OCR) or any other suitable image analysis process to analyze the one or more images of the detection feature 214 captured by the imaging component. Based at least in part on the analysis of the image(s) of the detection feature 214, the system 200 can detect (e.g., determine, predict, etc.) whether the patient has peritonitis. For example, as described in greater detail below regarding FIGS. 3A-6, the system 200 can be configured to use OCR to determine a measure of the visibility of the detection feature 214 through the waste solution 211 and, based at least in part on the measure of visibility, determine whether the one or more images obtained by the peritonitis sensor 203 indicate the presence of peritonitis in the patient.

In some embodiments, the system 200 can be configured to compare the peritonitis measurements obtained by the peritonitis sensor 203 to one or more reference peritonitis measurements. The reference peritonitis measurements can be stored in a database or memory (not shown) of or operably associated with and/or communicatively connected to the system 200 (e.g., to the processor and/or the controller of and/or operably associated with the system 200). Additionally, or alternatively, the system 200 can be configured to compare die peritonitis measurements with each other (e.g., to compare a first peritonitis measurement with a second peritonitis measurement).

The reference peritonitis measurements may be associated with a specific drain bag or APD system. In at least some embodiments, for example, the drain bag 206 can include a drain bag identifier 217 on the first side 206a and/or the second side 206b of the drain bag 206. The drain bag identifier 217 can include one or more numbers, letters, words, alphanumeric sequences, barcodes, QR codes, and/or any other suitable drain bag identifier. The drain bag identifier 217 can be associated with the reference peritonitis measurements for a given detection feature 214. For example, in some embodiments the drain bag identifier 217 can be input into the system 200 to access (e.g., identify, retrieve, etc.) the reference peritonitis measurements. Additionally, or alternatively, the drain bag identifier 217 can include one or more of the reference peritonitis measurements directly on the drain bag 206.

Although FIG. 2 depicts a drain bag 206 including a single detection feature 214, drain bags 206 configured in accordance with other embodiments of the present technology can include more detection features. For example, the drain bag 206 can include at least two, three, four, or any other suitable number of detection features 214. Additionally, or alternatively, although FIG. 2 depicts a system including a single peritonitis sensor 203, in other embodiments the system 201) can include more peritonitis sensors. In at least some embodiments, for example, the system 200 can include at least two, three, four, or any other suitable number of peritonitis sensors 203.

Figure 3A:
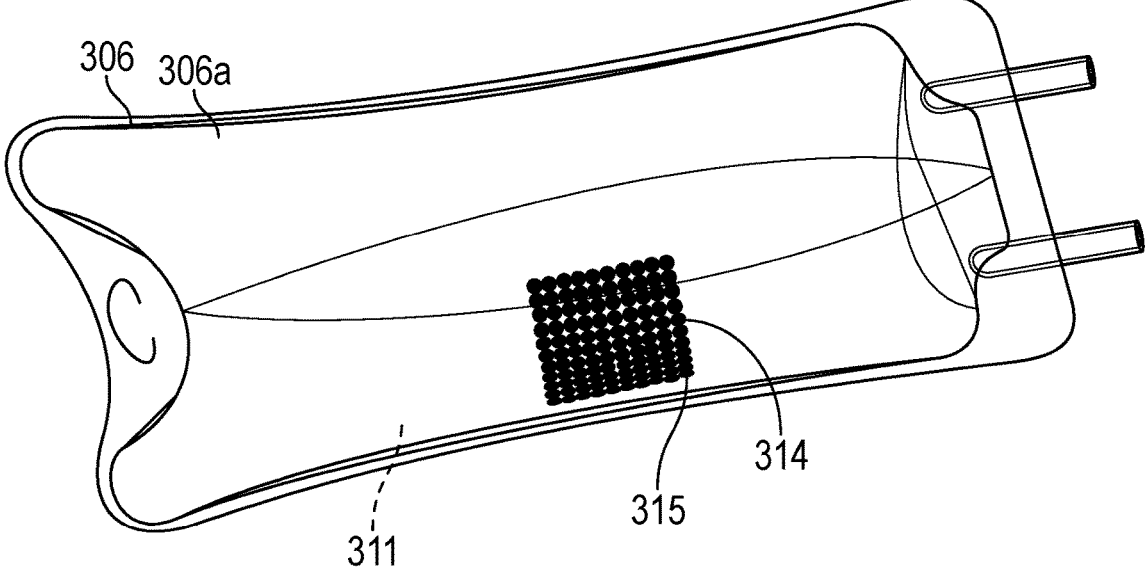
FIGS. 3A and 3B are partially schematic, perspective views of a drain bag configured in accordance with various embodiments of the present technology.
Figure 3B:
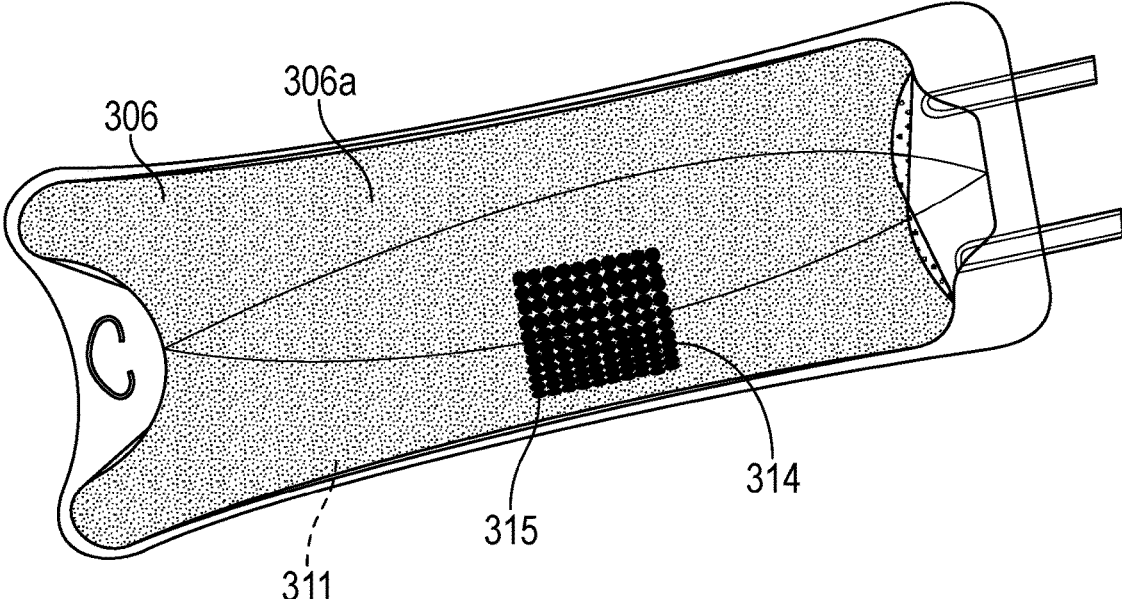

FIGS. 3A and 3B are partially schematic perspective views of a drain bag 306 configured in accordance with various embodiments of the present technology. Specifically, FIG. 3A illustrates the drain bag 306 at a first instance in which waste solution 311 in the drain bag 306 indicates that the patient does not have peritonitis, and FIG. 3B illustrates the drain bag 306 at a second instance in which the waste solution 311 indicates that the patient likely has peritonitis. The drain bag 306 can be generally similar to the drain bag 206 of FIG. 2. Accordingly, like numbers (e.g., waste solution 311 versus the waste solution 211 of FIG. 2, detection feature 314 versus detection feature 214, etc.) are used to indicate similar components, and the discussion of FIGS. 3A and 3B will be limited to features that differ from the drain bag 206 of FIG. 2 or are provided for context. Additionally, any features described with reference to the drain bag 306 can be combined with the features of the drain bag 206 of FIG. 2, and/or any other suitable drain bag described herein.

Consistent with the description of FIG. 2 above, the waste solution 311 of FIGS. 3A and FIG. 3B can change or alter the visibility of a detection feature 314 included on the drain bag 306 when peritonitis is present in a patient's abdomen. Here, the detection feature 314 is a pattern of dots 315. In FIG. 3A, for example, the waste solution 311 is clear, transparent, or non-diffusive such that the detection feature 314 (e.g., the pattern of dots 315 and/or the number of dots 315 in the pattern) is, readily visible through the drain bag 306 and the waste solution 311. In contrast, the waste solution 311 in FIG. 3B is darkened, diffusive, "cloudy," or less transparent in comparison to the waste solution 311 of FIG. 3A. As a result, the detection feature 314 in FIG. 3B is not as readily visible through the drain bag 306 and the waste solution 311, and/or the waste solution 311 can change the appearance of the detection feature 314. The changed appearance of the detection feature 314 can be used to detect or determine that a patient likely has peritonitis. For example, the darkening, diffusivity, or decrease in transparency of the waste solution 311 can obscure or make it difficult to accurately determine the number of dots 315 in the detection feature 314 of FIG. 3B, which can be used an indicator of peritonitis within the patient's abdomen. More specifically, the darkening, diffusivity, or decrease in transparency can be at least partially caused by the presence of bacteria or other indicia in the waste solution 311 that is associated with and or causing, a peritonitis infection in the patient. In other words, relative to a clearer or more transparent waste solution 311, a darker, more diffusive, or less transparent (e.g., more opaque) waste solution 311 can correspond to an increased amount of bacteria and/or an increased likelihood of peritonitis.

By way of example, a peritonitis detection procedure will now be described with reference to FIGS. 3A and 3B. As discussed above, the detection feature 314 includes a plurality of circles or dots 315 arranged in a square pattern. Because the waste solution 311 in FIG. 3A is generally or substantially transparent and does not interfere with visualization of the detection feature 314, each of the dots 315 appears spaced apart from the corresponding one or more neighboring dots, such that each individual dot 315 can be identified and/or counted. Accordingly, it is expected that a peritonitis sensor (such as the peritonitis sensor 203 of FIG. 2) observing the detection feature 314 presented in FIG. 3A could capture an image of the detection feature 314 such that each of the individual dots 315 could be identified within the image and/or such that a correct count of the number of dots 315 in the detection feature 314 can be determined. The ability to identify each individual dot 315 and/or determine a correct count of the dots 315 through the drain bag 306 and the waste solution 311 can indicate that the patient likely does not have peritonitis.

Referring to FIG. 3B, the darkening, diffusivity, or reduced transparency of the waste solution 311 has caused several of the dots 315 of the detection feature 314 to appear generally or substantially overlapped with the one or more neighboring dots 315, This can make it difficult to identify each of the individual dots 315 and/or to determine an accurate count of the dots 315. Accordingly, it is expected that the peritonitis sensor 203 will not be able to capture an image of the detection feature 314 from which each of the individual dots 315 can be identified and/or accurately counted. In turn, an incorrect count of the number of dots 315 in the detection feature 314 can indicate that the patient likely has peritonitis. In some embodiments, the likelihood of peritonitis can correspond to a degree and/or a type of a reduction in one or more properties of the capture image(s) of the detection feature 314. In at least some embodiments, for example, the increased darkening or diffusivity of the solution 311 in the drain ban 306 will cause a reduction of an intensity, spatial resolution, and/or spatial contrast of features of or elements in the captured image(s) of the detection feature 314. The amount or degree of the reduction(s) can indicate whether a patient likely has peritonitis.

Although the dots 315 of the detection feature 314 illustrated in FIG. 3B are shown as overlapping one another in response to the presence of the darkened or less transparent waste solution 311 in the drain bag 306, in other embodiments of the present technology the dots 315 can appear hazy, can disappear, or can have arty other suitable change in appearance in response to the presence of the darkened or less transparent waste solution 311 in the drain bag 306. Furthermore, although, the detection feature 314 of FIGS. 3A and 3B is a pattern of discs or circles, the detection feature 314 in other embodiments can include a pattern of triangles, squares, rectangles, pentagons, hexagons, line segments, rectilinear shapes, curvilinear shapes, and/or any other suitably-shaped objects. Additionally, or alternatively, although in the illustrated embodiment the pattern of the detection feature 314 is a square pattern of a plurality of shapes, the pattern of the detection feature 314 in other embodiments can be a circular pattern, a triangular pattern, a square pattern, a rectangular pattern, a pentagonal pattern, a hexagonal pattern, a linear pattern, a rectilinear pattern, a curvilinear pattern, and/or any other suitable pattern.

Continuing with the example of FIGS. 3A and 3B, a system configured in accordance with the present technology (e.g., the system 100 of FIG. 1 and/or the system 200 of FIG. 2) can process images of the detection feature 314 captured by a peritonitis sensor (e.g., the peritonitis sensor 103 of FIG. 1 and/or the peritonitis sensor 203 of FIG. 2) to determine whether the patient likely has peritonitis. For example, the system can compare a first image of the detection feature 314 captured in the absence of waste solution 311 with a second image of the detection feature 314 in the presence of waste solution 311. In some embodiments, the first image of the drain hag 306 can be a reference image (e.g., a reference peritonitis measurement as described above with respect to FIG. 2). Additionally, or alternatively, the system can compare a third image of the detection feature 314 in the presence of clear or transparent solution (e.g., the waste solution 311 of FIG. 3A) to the second image. Comparing the images can include determining a similarity of the detection feature 314 between the images. As a specific example, the system can determine a first count of the dots 315 from the first and/or third images, determine a second count of the dots 315 from the second image, and compare the first number of the dots 315 to the second number of the dots 315. If the second count varies front the first count by more than a threshold limit, the system can determine that the patient likely has peritonitis. In some embodiments, the threshold can be a variance in the number of dots 315 between about 10% and about 95%, such as at least 10%, 20%, 30%, 40%, 50%, 60%, 70%, 80%, 90%, or any other suitable percent difference. In at least some embodiments, for example, all of the dots 315 will be countable in the second image when the patient does not have peritonitis, and only a subset (e.g., a few, less than all, etc.) or none of the dots 315 will be countable in the second image when the patient likely has peritonitis.

In some embodiments, comparing the images can include comparing one or more properties (e.g., intensity, spatial contrast, spatial resolution, etc.) of the detection feature 314 between images of the detection feature 314. As a specific example, the system can determine a property (e.g., a contrast or resolution) of the detection feature 314 in the first and/or third images of the detection feature 314, determine the same property (e.g., the contrast or resolution) of the detection feature 314 in the second image of the detection feature 314, and compare the property between the images. If the property in the second image varies from the property in the first and/or third images by more than a threshold limit, the system can determine that the patient likely has peritonitis. The thresholds can be the same or similar to the thresholds discussed in the count of dots 315 example above.

Figure 4:
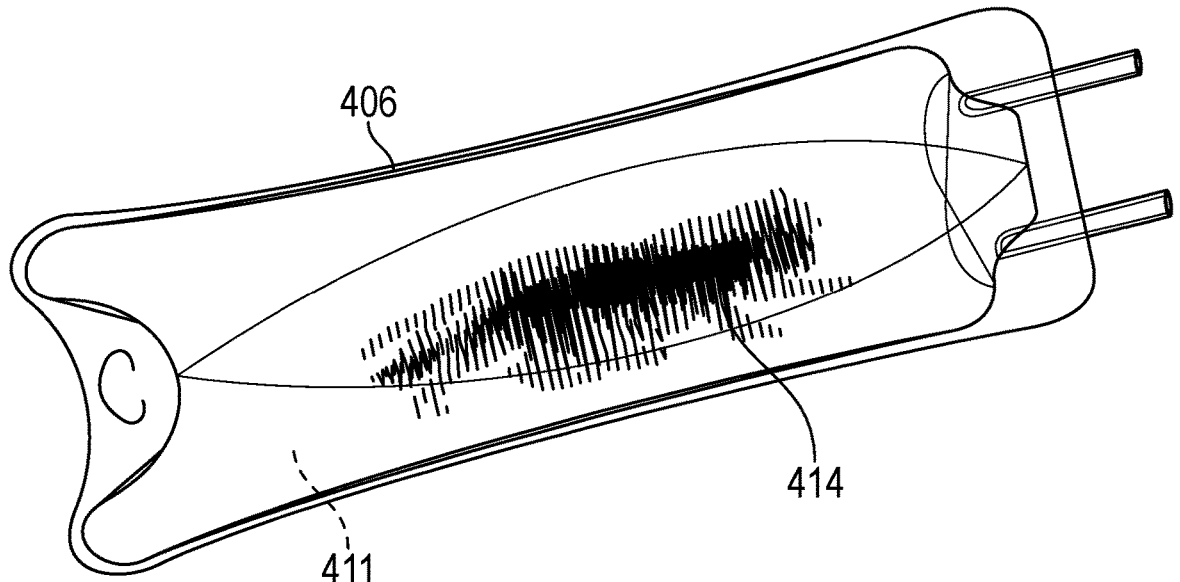
FIGS. 4 and 5 illustrate respective partially schematic, perspective views of additional drain bags, each configured in accordance with various embodiments of the present technology.
Figure 5:
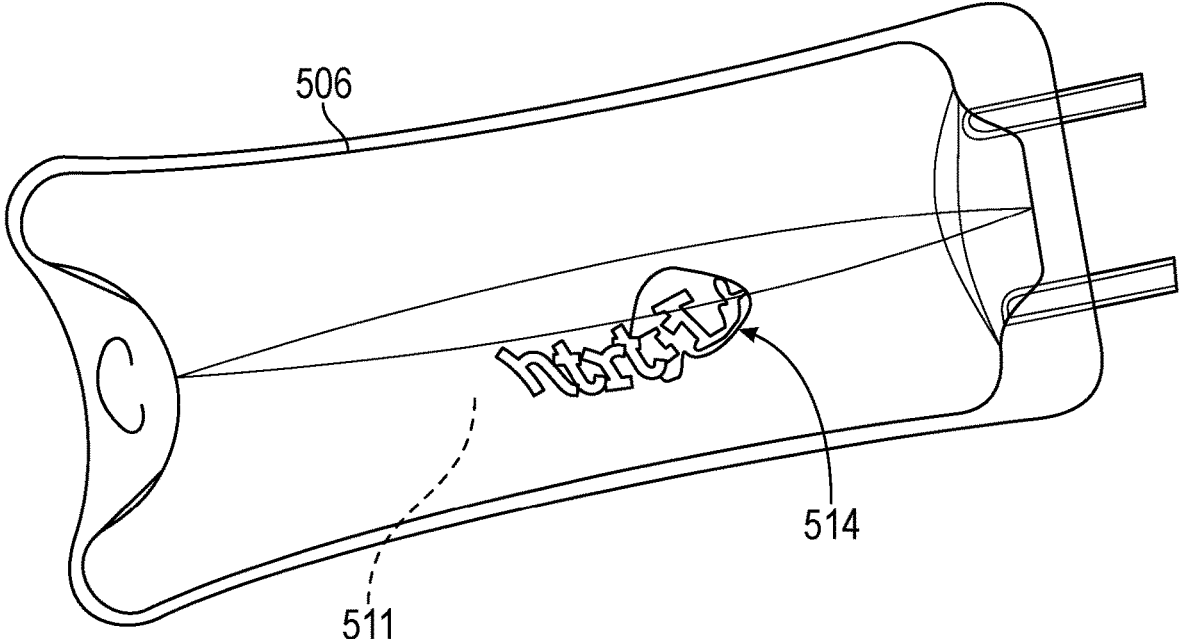

Additionally, or alternatively, the drain bag 306 of FIGS. 3A and 3B can include an identifier (e.g., the identifier 217 of FIG. 2). In these embodiments, a correct count of the dots 315 of the detection feature 314 can be stored in a database (not shown) and associated with identifier of the drain bag 306. Thus, when the system determines a count of the dots 315 in the detection feature 314 from the second image described above, the system can (a) retrieve the correct count of the dots 315 from the database based at least in part on the identifier of the drain bag 306, and (b) compare the count determined from the second image to the correct count retrieved from the database. The system can further determine that the patient likely has peritonitis when the counts differ by more than the threshold amount or percentage, Stated another way, the system can further determine that the patient likely does not have peritonitis when the counts do not differ by more than the threshold amount or percentage, FIGS. 4 and 5 are partially schematic, perspective views of additional drain bags 406 and 506, respectively, each configured in accordance with various embodiments of the present technology. The drain bags 406 and 506 can be generally similar to the drain bag 306 of FIGS. 3A and 3B, the drain bag 206 of FIG. 2, and/or the drain bag 106 of FIG. 1. Accordingly, like numbers (detection feature 414, 514 versus the detection feature 214, 314 of FIGS. 2, 3A and 3B) are used to indicate like elements, and the discussion of FIGS. 4 and 5 will be limited to those features that differ from the drain bag. 306 of FIG. 3 or are provided for context. Additionally, any features described with reference to the drain bags 406, 506 can be combined with the features of the drain bags 106, 206, 306 of FIGS. 1-3B, and/or any other suitable drain bag described herein.

Referring first to the embodiment illustrated in FIG. 4, the detection feature 414 included on the drain bag 406 includes an optical illusion graphic element ("optical element"). The optical element is configured as an animal in one or more stances or states (e.g., standing, sitting, walking, running, sprinting, etc.). In other embodiments, the optical element can include any other suitable optical element having one or more states.

A darkening or reduction in transparency of the waste solution 411 can alter an appearance of the optical element from a first appearance (e.g., a first stance or state) to a second appearance (e.g., a second stance or state). In the illustrated embodiment, for example, the animal in the optical element of the detection feature 414 can appear to be running in the absence of the waste solution 411 and/or in the presence of generally transparent waste solution 411. In the presence of darkened, cloudy, or less transparent waste solution 411, however, the animal in the optical element of the detection feature 414 can appear to be stationary or standing. The state or stance of the optical element can be identified (e.g., by an operator, by the system via images of the detection feature captured by a peritonitis sensor, etc.) to determine whether the patient likely has peritonitis. In some embodiments, the system can automatically identify the state or stance of the optical element and determine whether the state or stance indicates the presence of peritonitis. In such embodiments, the system can be preprogrammed with information (e.g., reference peritonitis measurements, reference images, instructions, etc.) correlating the one or more states or stances of the animal in the optical element to the presence or absence of peritonitis. In some embodiments, the operator of the system can identify the state or stance and/or enter the state or stance into the system, and/or the operator or the system can then determine whether the state or stance indicates the presence of peritonitis.

Referring next to the embodiment illustrated in FIG. 5, the detection feature 514 includes text. The text can include CAPTCHA-style text, or any other suitable text. A darkening or reduction of transparency of the waste solution 511 can change the appearance of the text, and can cause the text to, for example, become blurry, cloudy, hazy, or difficult to read. As a specific example, the darkening or reduction in transparency of the waste solution 511 can reduce the accuracy with which the system can identify and/or read the text of the detection feature 514 (e.g., via OCR) from images of the detection feature 514 captured by a peritonitis sensor. For example, an identification or reading of the text from an image of the detection feature 514 can be compared against a reference identification or reading of the text. When a difference between the identification or reading of the text differs from the reference identification or reading of the text by more than a threshold amount or percentage, the system can determine that the patient likely has peritonitis.

Figure 6:
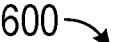
FIG. 6 is a partially schematic, perspective view of another APD system configured in accordance with various embodiments of the present technology.

FIG. 6 is a partially schematic representation of an APD system 600 ("the system 600") configured in accordance with various embodiments of the present technology. The system 600 can be generally similar to the systems 100 and/or 200 of FIGS. 1 and 2. Accordingly, like numbers (e.g., peritonitis sensor 603 versus the peritonitis sensor 103, 203 of FIGS. 1 and 2) are used to indicate like elements, and the discussion of the system 600 will be limited to those features that differ from the system 200 of FIG. 2 or are provided for context. Additionally, any features described with reference to the system 600 can be combined with one or more features of the system 100 of FIG. 1 or the system 200 of FIG. 2.

The system 600 includes a display or screen 622 positioned within a field of view of the peritonitis sensor 603. In the illustrated embodiment, the display 622 is coupled or mounted to a second shelf 618b of a support structure 618. In other embodiments, the display 622 can have any other suitable position relative to the support structure 618. The display 622 can be configured to display a detection feature 614 (e.g., as opposed to the detection feature 614 being included on, a drain bag). In some embodiments, the display 622 is an electronic display (e.g., a video display) and the detection feature 614 is a displayed image generated by a computer processor (e.g., the processor 101a). In some embodiments, the display 622 is a flat, back-lit panel on which the detection feature 614 is opaquely applied by printing or any other suitable process or method. In some embodiments, the display 622 is a flat panel containing one or more illuminating elements (e.g., LEDs) positioned and/ or configured to form the detection feature 614. In some embodiments, the display 622 is an opaque flat panel with a surface having a selected color or brightness on which the detection feature 614 is applied by printing (or any other suitable process or method) in a contrasting color or brightness, and where illumination of the detection feature 614 is externally supplied to the display 622. In other embodiments, the display 622 can include any other suitable devices, systems, or techniques for displaying or otherwise presenting the detection feature 614 (e.g., to the peritonitis sensor 603).

The system 600 further includes a drain bag 606 positioned between the display 622 and the peritonitis sensor 603. The peritonitis sensor 603 can be configured to obtain peritonitis measurements (e.g., images) of the detection feature 614 shown on the display 622 through the drain bag 606 and/or waste solution 611 contained therein. Accordingly, the system 600 can use the peritonitis measurements to detect peritonitis, as described previously and with reference to FIGS. 2-5.

The detection feature 614 can include any of the detection features described herein, including those shown and described with reference to FIGS. 3A-5. In some embodiments, the display 622 can be configured to display one or more detection features 614 (e.g., simultaneously, in sequence, etc.). Although the system 600 includes a single display 622 in the illustrated embodiment, the system 600 can include more displays in other embodiments of the present technology, such as two, three, four, or more displays.

Figures 7, 8:
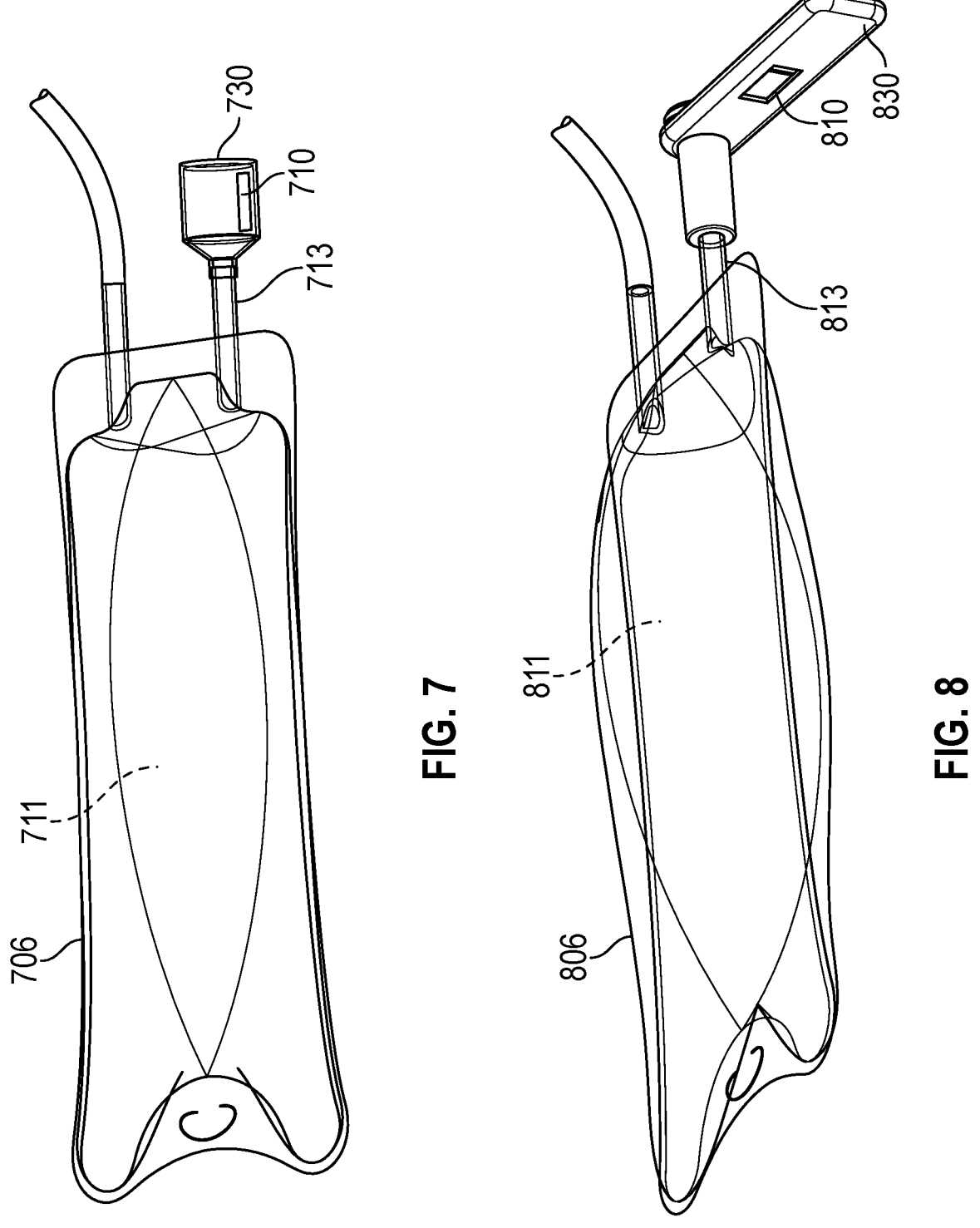
FIG. 7 is a partially schematic, perspective view of a drain bag and a diagnostic device, each configured in accordance with various embodiments of the present technology.
FIG. 8 is a partially schematic, perspective view of a drain bag and another diagnostic device, each configured in accordance with various embodiments of the present technology.

FIGS. 7 and 8 are partially schematic, perspective views of drain bags 706 and 806 and diagnostic devices 730 and 830 respectively, configured in accordance with various embodiments of the present technology. The diagnostic devices 730, 830 can be generally similar to the diagnostic device 130 of FIG. 1. Additionally, or alternatively, the respective drain bags 706, 806 of FIGS. 7 and 8 can be generally similar to the drain bags 206, 306, 406, 506, and/or 606 of FIGS. 2-6. Accordingly, like numbers (waste solution 711, 811 versus the waste solution 211, 311, 411, 511, 611 of FIG. 2-6) are used to indicate like elements, and the discussion of FIGS. 7 and 8 will be limited to those features that differ from the drain bag 206 of FIG. 2 or are provided for context. Additionally, any features described with reference to the embodiments illustrated in FIGS. 7 and 8 can be combined with one or more features of the embodiments illustrated in FIGS. 1-6, and or any other embodiment described herein.

Referring to FIGS. 7 and 8 together, the diagnostic devices 730, 830 can be fluidly coupled to the respective drain bags 706, 806 via respective ports or couplings 713, 813, such that each of the diagnostic devices 730, 830 can receive waste solution 711, 811 from the respective drain bag 706, 806. The diagnostic devices 730, 830 can be coupled or attached to the respective drain bags 706, 806 at any point before, during or after a therapy session (e.g., by a patient, a clinician, an operator, etc.). In at least some embodiments, the drain bags 706, 806 and diagnostic devices 730, 830 can interchangeable, such that the diagnostic device 730 can be coupled to the drain baa 806, and the diagnostic device 830 can be, coupled to the drain bag 806, In other embodiments, the diagnostic devices 730, 830 can be integrated into or otherwise form a single-piece assembly with the respective drain bags 706, 806.

In some embodiments, the diagnostics devices 730, 830 are single-use devices and/or can be a portion of a disposable set. In such embodiments, including the diagnostic devices 730, 830 in the disposable set is expected to prevent or reduce the likelihood that a patient reuses the diagnostic devices 730, 830 to test for peritonitis. It is expected that this will reduce the likelihood of a false positive and/or a false negative determination of peritonitis.

The diagnostic devices 730, 830 can include respective test strips 710, 810 configured to detect peritonitis. In at least some embodiments, for example, the test strips 710, 810 (e.g., an indicator of the test strips 710, 810) can be configured to react (e.g., chemically react, change color, etc.) to one or more indicia (e.g., bacteria, etc.) associated with peritonitis. The presence or absence of peritonitis can be determined based at least in part on the reaction (or lack thereof) of the test strips 710, 810 (e.g., by reading or otherwise observing the test strips 710, 810). In some embodiments, the test strips 710, 810 can each include one or more Cytur® test strips, PERiPLEX® test strips, and/or any other suitable test strips.

Figure 9:
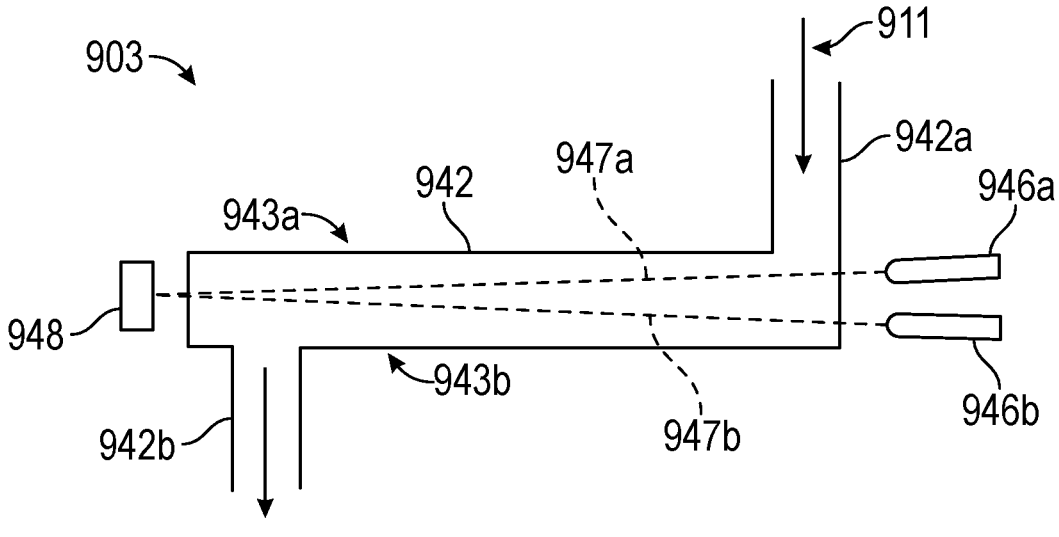
FIG. 9 is a partially schematic side view of a peritonitis sensor in operation and configured in accordance with various embodiments of the present technology.

FIG. 9 is a partially schematic, side view of another peritonitis sensor 903 configured in accordance with various embodiments of the present technology. The peritonitis sensor 903 includes one or more light sources or lighting elements 946 (identified individually as first lighting element 946*a* and second lighting element 946*b* in FIG. 9) and one or more optical detectors or light-detecting elements 948. In some embodiments, the lighting elements 946 can be LEDs, LED strips, one or more lasers, and/or any other suitable tight sources, Each of the lighting elements 946 can be configured to emit tight at one or more wavelengths and/or intensities. In some embodiments, the lighting elements 946 can be configured to pulse or "blink" such that the lighting elements 946 are "on" (e.g., emit light at a first wavelength and/or intensity) for a first length of time and are "off" (e.g., emit light at a second wavelength and/or intensity, or do not emit light) for a second length of time. In these and other embodiments, the light-detecting element(s) 948 can be photoreceptors, photodiodes, or other light-sensitive elements. In some embodiments, each of the light-detecting elements 948 can correspond to a specific wavelength (e.g., color) of light. Although the peritonitis sensor 903 is shown as including two lighting elements 946 in FIG. 9, the peritonitis sensor 903 can include more than two or a single lighting element in other embodiments of the present technology. Additionally, or alternatively, the peritonitis sensor 903 can include more than one light-detecting element 948 (e.g., a respective light-detecting element for each lighting element) in other embodiments.

Also shown in FIG. 9 is an elongate body 942 or lumen positioned between the lighting elements 946 and the light-detecting element(s) 948. The elongate body 942 can be at least transparent and/or at least partially translucent. The elongate body 942 includes a first end portion 942*a* (e.g., inlet, inflow, etc.) and a second end portion 942*b* (e.g., outlet, outflow, etc.) downstream from and opposite the first end portion 942*a*. The elongate body 942 can be at least partially or fully hollow, such that solution 911 can enter the elongate body 942 via the first end portion 942*a*, flow between the lighting elements 946 and the light-detecting element(s) 948 of the peritonitis sensor 903, and exit the elongate body 942 via the second end portion 942*b*.

In some embodiments, the first end portion 942*a* can be fluidly coupled to and configured to receive solution 911 from a cassette (e.g., the cassette 104 of FIG. 1) of an APD system and/or a transfer set or catheter (e.g., the catheter 109 of FIG. 1). The second end portion 942*b* can be fluidly coupled to a drain bag of an APD system, such as the drain bag 106 of FIG. 1, or any other suitable drain bag. Accordingly, in some embodiments, the peritonitis sensor 903 can be positioned (a) downstream of the cassette 104, the transfer set, and/or the catheter, and (b) upstream of the drain bag. In other embodiments, the peritonitis sensor 903 can have any other suitable position in the APD system. In at least some embodiments, for example, the elongate body 942 can be part of a cassette of an APD system, such as the cassette 104 of FIG. 1, such that the peritonitis sensor 903 can be aligned with the cassette 104. In these and other embodiments, the elongate body 942, the first end portion 942*a*, and/or the second end portion 942*b* can be fluid lines of a disposable set (e.g., the disposable set 107 of FIG. 1) and/or otherwise configured for inline peritonitis detection (e.g., to detect peritonitis via fluid flowing through the disposable set).

In the illustrated embodiment, the lighting element(s) 946 are positioned proximate a first end or side of the elongate body 942, and the light-detecting element 948 is positioned proximate a second, opposite end or side the elongate body 942. In other embodiments, the lighting element(s) 946 and the light-detecting element(s) 948 can have any other suitable position relative to the body 942. For example, the lighting element(s) 946 can be positioned proximate the second end or side and the light-detecting element(s) 948 can be positioned proximate the first end or side. Additionally, or alternatively, the lighting element(s) 946 and/or the light-detecting element(s) 948 can be angled relative a longitudinal axis of the elongate body 942.

The lighting element(s) 946 can be configured to emit light 947 (shown in dashed lines in FIG. 9) through the solution 911 in the elongate body 942 and toward the light-detecting element 948. In the illustrated embodiment, for example, the first lighting element 946*a* and the second lighting element 946*b* are configured to emit first light 947*a* and second light 947*b* through the solution 911 and toward the light-detecting element 948. The first lighting element 946*a* can be a first laser such that the first light 947*a* is a first beam of light. Additionally, or alternatively, the second lighting element 946*b* can be a second laser such that the second light 947*b* is a second beam of light. The first light 947*a* and the second light 947*b* can be generally similar, the same, or different. As a specific example, the first light 947*a* has a frequency corresponding to blue light and the second light 947*b* has a second frequency corresponding to red light.

The light-detecting element 948 can be configured to detect the light 947 emitted from the lighting element(s) 946. An amount of light 947 detected by the light-detecting element 948 can be used to determine whether a patient likely has peritonitis. In at least some embodiments, for example, the presence of one or more indicia of peritonitis in the solution 911 can reduce the amount of light 947 detected by the light-detecting element 948. The one or more indicia can include white blood cells, red blood cells, bacteria, and/or any other suitable indicia.

The first light 947*a* and the second light 947*b* shown in FIG. 9 can have different scattering (e.g., reflection, refraction, etc.) or light-absorption properties (e.g., in response to the one or more indicia in the solution 911). In the illustrated embodiment, for example, white blood cells in the solution 911 can scatter or absorb the first (e.g., blue) light 947*a* and the second (e.g., red) light 947*b* equally. In these and other embodiments, red blood cells in the solution 911 can scatter or absorb more of the first (e.g., blue) light 947*a* than of the second (e.g., red) light 947*a*. Accordingly, generally or substantially equal scattering of both the first light 947*a* and the second light 947*b*, as determined by a reduced amount of the first light 947*a* and the second light 947*b* detected by the light-detecting element 948, can be associated with the presence of relatively large quantities of white blood cells in the solution 911 flowing through the elongate body 942, and can indicate the presence of peritonitis in the patient. The scattering, however, of only the first light 947*a* or the second light 947*b*, as determined by a reduced amount of the first light 947*a* or the second light 947*b* detected by the light-detecting element 948, can be associated with the absence of peritonitis in the patient.

The structure of the elongate body 942 can affect the sensitivity of the peritonitis sensor 903. For example, as the elongate body 942 becomes more elongated, a greater amount of fluid can be positioned between the lighting element(s) 946 and the light-detecting element(s) 948. As such, the probability that indicia (e.g., white blood cells, red blood cells, bacteria, and/or any other suitable indicia) of peritonitis intersect the path(s) of the first light 947$a$ and/or the second light 947$b$ at some point between the lighting element(s) 946 and the light-detecting element(s) 948 increases even when the solution contains a small amount of indicia, meaning that the likelihood that the first light 947$a$ and/or the second light 947$b$ is scattered by the indicia before it reaches the light-detecting element(s) 948 increases. In other words, increasing the length of the elongate body 942 can increase the sensitivity of the peritonitis sensor 903 while decreasing the length of the elongate body 942 can decrease the sensitivity of the peritonitis sensor 903.

The scattering of the first and second lights 947$a$, 947$b$ detected by the light-detecting elements) 948 can be compared against one or more reference measurements. This can be similar to the comparison described previously and with reference to FIGS. 3A and 3B. For example, a system (e.g., the system 100 of FIG. 1) can compare a first reading from the light-detecting element(s) 948 captured in the absence of waste solution 911 with a second reading from the light-detecting element(s) 948 in the presence of waste solution 911. In some embodiments, the first reading of the light-detecting element(s) 948 can be a reference reading (e.g., a reference scattering reading, similar to the reference peritonitis measurement described above with respect to FIG. 2). Additionally, or alternatively, the system can compare a third reading from the light-detecting element(s) 948 in the presence of clear or transparent solution to the second reading. Comparing the readings can include determining a similarity of the readings. As a specific example, the system can determine a first intensity of the first and second lights 947$a$, 947$b$ from the first and/or third readings, determine a second intensity of the first and second lights 947$a$, 947$b$ from the second reading, and compare the first intensity to the second intensity. If the second intensity varies from the first intensity by more than a threshold limit, the system can determine that the patient likely has peritonitis. In some embodiments, the threshold can be a variance in the intensities between about 10% and about 95%, such as at least 10%, 20%, 30%, 40%, 50%, 60%, 70%, 80%, 90%, or any other suitable percent, difference.

As described previously, in some embodiments the lighting element(s) 946 and or the light-detecting element(s) 948 cart be angled relative to the longitudinal axis of elongate body 942. As a specific example, in some embodiments the peritonitis sensor 903 includes (a) a single lighting element 946 positioned proximate the first or second end portions 942$a$, 942$b$, and (b) one or more light-detecting element(s) 948 each positioned at a respective angle relative to the longitudinal axis elongate body 942 (e.g., at a respective angle relative to the light 947 emitted by the single lighting element 946). In these and other embodiments, the light-detecting element(s) can detect an intensity, a phase, a color, a lime-of-flight, and/or a change in the intensity, phase, color, and/or time-of-flight, of the light 947 scattered or otherwise reflected by the solution 911.

In some embodiments, the elongate body 942 can be a portion of a drain bag of an APD system, such as any of the drain bags 106, 206, 306, 406, 506, 606, 706, 806 of FIGS. 1-8. In such embodiments, the Wining elements 946 can be positioned on a first side of the elongate body 942 (e.g., a first side of the drain bag, such as the first side 206$a$ of the drain bag 206) and the light-detecting element(s) 948 can be positioned on a second side of the elongate body 942 opposite the first side (e.g., a second side of the drain bag, such as the second side 206$b$ of the drain bag 206). Light 947 emitted by the lighting elements 946 can pass through the first and second sides of the elongate body and be detected by the light-detecting element(s) 948. In these and other embodiments, the solution 911 can be generally or substantially flowing or stationary (e.g., not flowing) when the peritonitis measurements are captured by the light-detecting element(s) 948.

Figure 9A:
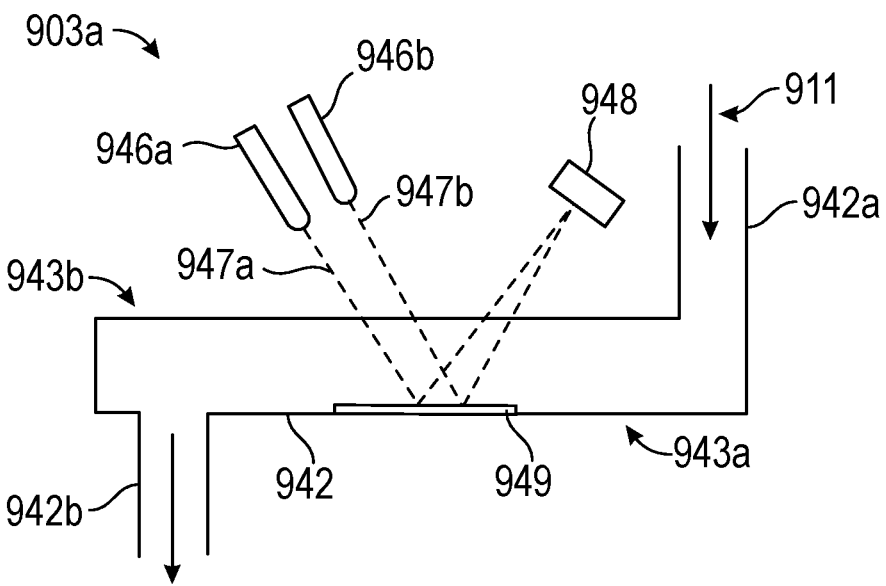
FIG. 9A is a partially schematic, side view of another peritonitis sensor in operation and configured in accordance with various embodiments of the present technology.

FIG. 9A is a partially schematic, side view of another peritonitis sensor 903$a$ configured in accordance with various embodiments of the present technology. The peritonitis sensor 903$a$ can be generally similar to the peritonitis sensor 903 of FIG. 9 except that the peritonitis sensor 903$a$ can include one or more reflective elements 949 (e.g., mirrors). The reflective element(s) 949 can be positioned proximate a first side 943$a$ of the elongate body 942 (e.g., at least partially within the elongate body 942, or on an exterior of the elongate body 942). The lighting element(s) 946 and the light-detecting element(s) 948 can be positioned proximate a second side 943$b$ of the elongate body 942, opposite the first side 943$a$. The reflective element 949 can be positioned, centered, aligned with, and/or held at a fixed distance from the lighting element(s) 946 and the light-detecting elements) 948. In some embodiments, the elongate body 942 can be a fluid line, a portion of a drain bag, a portion of a cassette, or a portion of a damping device of an APD system.

In operation, the light(s) 947 emitted from the lighting element(s) 946 can pass at least partially through the elongate body 942 (e.g., and any solution 911 within or flowing therethrough) toward the reflective element(s) 949, and can be reflected by the reflective element(s) 949 toward the light-detecting element(s) 948 at least partially through the elongate body 942 (e.g., and any solution 911 within or flowing therethrough). Accordingly, the light(s) 947 can scatter when peritonitis indicia are present in the solution 911 such that amounts of the light(s) 947 detected by the light-detecting element(s) 948 can indicate the likelihood of peritonitis being present within the patient, similar to the operation the peritonitis sensor 903 described above with respect to FIG. 9.

Figure 10:
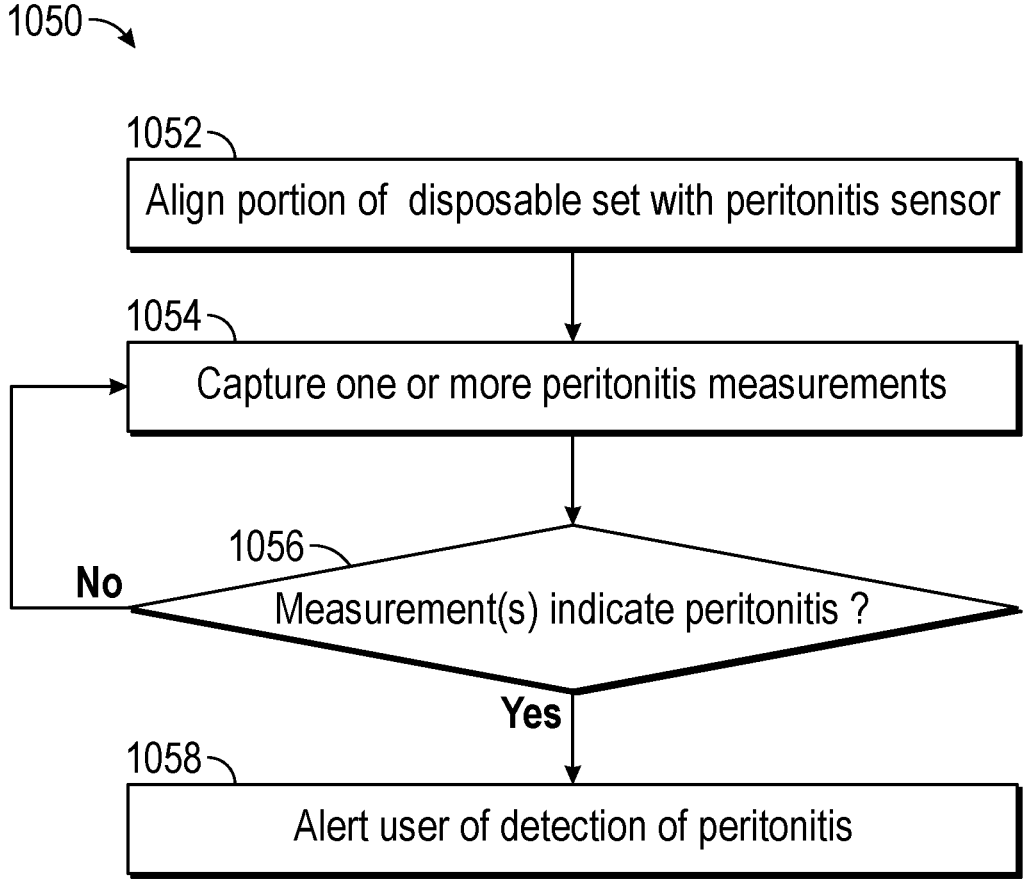
FIG. 10 is a flow diagram illustrating a method of detecting peritonitis in accordance with various embodiments of the present technology.

FIG. 10 is a flow diagram illustrating a method 1050 of detecting peritonitis in accordance with various embodiments of the present technology. The method 1050 is illustrated as a set of blocks, steps, operations, or processes 1052-1058. All or a subset of the blocks 1052-1058 can be executed at least in part by various components of a system, such as the APD system 100 of FIG. 1. For example, all or a subset of the blocks 1052-1058 can be executed at least in part by a pump, a peritonitis sensor, a cassette, a drain bag, a diagnostic device, fluid lines, and/or other portions of a disposable set. Additionally, or alternatively, all or a subset of the blocks 1052-1058 can be executed at least in part by an operator (e.g., a user, a patient, a caregiver, a family member, a physician, etc.) of the system. Furthermore, any one or more of the blocks 1052-1058 can be executed in accordance with the discussion above. Many of the blocks 1052-1058 of the method 1050 are discussed in detail below with reference to FIGS. 2-9A for the sake of clarity and understanding.

The method 1050 begins at block 1052 by aligning a portion of a disposable set with a peritonitis sensor or diagnostic device. In some embodiments, aligning the portion of the disposable set with a peritonitis sensor can include aligning a detection feature with (e.g., into a field of view of) the peritonitis sensor. The detection feature can be similar to the detection features discussed above with respect to FIGS. 2-6. For example, FIG. 2 illustrates the detection feature 214 included on the drain bag 206 and at least partially aligned with the peritonitis sensor 203. The support structure 218 can be employed to stably and removably position the detection feature 214 in a fixed position and/or orientation as part of the alignment process. For example, an operator can position the drain bag 206 on the second shelf 218*b* of the support structure 218 such that the first side 206*a* of the drain bag 206 is positioned at least partially between the peritonitis sensor 203 and the detection feature 214. In some embodiments, the second side 206*b* of the drain bag 206 can include the detection feature 214, in other embodiments, the detection feature can be displayed on a display screen, similar to how the detection feature 614 is displayed on the display screen 622 of FIG. 6. Referring again to FIG. 2, an operator can position the peritonitis sensor 203 on the first shelf 218*a* of the support structure 218 before, during, or after placing the drain bag on the second shelf. All or a subset of block 1052 can be performed without solution actively flowing through the disposable set and/or before the waste solution 211 enters the drain bag 206. Although described in the context of drain bag 206 of FIG. 2, it can be appreciated that the description of block 1052 applies equally to any of the drain bags described herein, and/or any other suitable drain bag.

In some embodiments, aligning the disposable set with a diagnostic device can include installing the diagnostic device on and/or fluidly coupling the diagnostic device with a portion of the drain bag. The diagnostic device can be similar to the diagnostic devices 730, 830 discussed above with respect to FIGS. 7 and 8. For example, FIGS. 7 and 8 illustrate the respective diagnostic devices 730, 830 aligned with and/or fluidly coupled to the corresponding ports 713, 813 of the respective drain bags 706, 806. All or a subset of block 1052 can be performed without a solution actively flowing through the disposable set and/or before the waste solution 711, 811 enters the respective drain bags 706, 806.

In some embodiments, aligning the disposable set with a peritonitis sensor can include aligning a portion of the disposable set with one or more lighting elements and a light-detecting element, for example, in a manner generally consistent with the discussion of FIGS. 9 and 9A above. For example, FIG. 9 illustrates one or more lighting elements 946 aligned with the light-detecting element 948. The elongate body 942 (e.g., a portion of a disposable set) is positioned between the lighting elements 946 and the light-detecting element 948 such that solution flowing through the elongate body 942 flows between the lighting elements 946 and the light-detecting element 948. All or a subset of block 1052 can be performed without a solution actively flowing through the disposable set and/or before the solution 911 enters the elongate body 942. As another example, FIG. 9A illustrates one or more lighting elements 946 and the light-detecting element 948 aligned with a reflective element 949. The reflective element 949 can be positioned proximate a first side 943*a* of the elongate body 942 (e.g., a portion of a disposable set), and the one or more lighting elements 946 and the light-detecting element 948 can be positioned proximate a second side 943*b* of the elongate body 942 opposite the first side 943*a*, such that solution flowing through the elongate body 942 flows between the reflective element 949 and the one or more lighting elements 946 and the light detecting element 948. All or a subset of block 1052 can be performed without a solution actively flowing through the disposable set and/or before the solution 911 enters the elongate body 942.

At block 1054, the method 1050 continues by capturing or obtaining one or more peritonitis measurements. In some embodiments, capturing the peritonitis measurement(s) can include using the peritonitis sensor to capture one or more images of the detection feature, such as the detection features described above with respect to FIGS. 2-6. For example, FIGS. 3A and 3B illustrate a detection feature 314 including a pattern having a number of dots 315. In such embodiments, block 1056 can include capturing an image of the detection feature 314 and counting or otherwise determining a number of dots 315 in the pattern. As another example. FIG. 4 illustrates a detection feature 414 including an optical element depicting an animal in a plurality of states or stances. In such embodiments, block 1056 can include, capturing one or more images of the optical element and determining a state or stance of the animal. As another example, FIG. 5 illustrates a detection feature 514 including text. In such embodiments, block 1056 can include capturing an image of the text and identifying or determining a reading of the text. Any of the detection features of FIGS. 2-5 can be displayed on a screen (e.g., as opposed to on a drain bag), such as the screen 622 of FIG. 6, such that capturing the peritonitis measurements can include displaying the detection features on the display or screen. In some embodiments, capturing the peritonitis measurement(s) can include using a diagnostic device to run one or more tests, such as with the diagnostic devices 730, 830 discussed above with respect to FIGS. 7 and 8. In some embodiments, capturing the peritonitis measurement(s) can include using a peritonitis sensor to detect an amount of light emitted from one or more lighting elements, such as with the light-detecting element 948 and the lighting element(s) 946 discussed above with respect to FIG. 9.

At block 1056, the method 1050 continues by determining whether the one or more peritonitis measurements captured in block 1054 indicate the presence of peritonitis in a patient. In some embodiments, determining whether the peritonitis measurement(s) indicate peritonitis can include using OCR, or any other suitable image analysis technique, to analyze a detection feature, such as the detection features described above with respect to FIGS. 2-6. For example, FIGS. 3A and 3B illustrate a detection feature 314 including a pattern having a number of dots 315. In such embodiments, block 1056 can including counting or otherwise determining a number of dots in the pattern, and comparing the determined number to a known or reference number of dots in the pattern to determine a difference. When the determined difference exceeds a threshold, the method 1050 can determine that peritonitis is likely present in the patient. Additionally, in some embodiments, block 1056 can including determining one or more properties of an image of the detection feature 314, and comparing the determined one or more properties to one or more reference image properties to determine a difference. When the determined difference exceeds a threshold, the method 1050 can determine that peritonitis is likely present in the patient. As another example, FIG. 4 illustrates a detection feature 414 including an optical element depicting an animal in one or more states or stances. In such embodiments, block 1056 can include identifying whether the optical element depicts the animal in a first state or stance (e.g., running) or in a second state or stance (e.g., stationary or standing). The method 1050 can determine that peritonitis is likely present in the patient when the method. 1050 identifies the second state or stance. As another example, FIG. 5 illustrates a detection feature 514 including text. In such embodiments, block 1056 can include comparing a reading of the text with known or reference reading of the text. When the readings differ by more than a threshold amount, the method 1050 can determine that peritonitis is likely present in the patient. In some embodiments, determining whether the peritonitis measurement(s) indicate peritonitis can include performing chemical reaction test using a test strip of a diagnostic device, such as the test strips 710, 810 described above with respect to FIGS. 7 and 8, and reading the test strips 710, 810 to determine whether the chemical reaction indicates peritonitis. In such embodiments, this can include waiting a predetermined amount of time before determining whether the peritonitis measurement(s) indicate peritonitis. The predetermined amount of time can be any suitable amount of time for the test strips 710, 810 to undergo the chemical reaction (e.g., in response to the presence of peritonitis). In some embodiments, determining whether the peritonitis measurement(s) indicate peritonitis can include using an optical detector to measure or detect an amount, intensity, and/or scattering of light through waste solution flowing through a portion of the disposable set, such as using the light-detecting element 948 described above with respect to FIGS. 9 and 9A. In such embodiments, the peritonitis measurement(s) can indicate peritonitis if the detected amount or intensity of the light is below a threshold limit and/or otherwise indicates that peritonitis is present in the patient.

When the measurements indicate that peritonitis is not likely present—in the patient (block 1056: No), method 1050 can return to block 1054 to capture additional measurements. Alternatively, method 1050 can end. On the other hand, when the measurements indicate that peritonitis is likely present in the patient (block 1056: Yes), method 1050 can proceed to block 1058.

At block 1058, the method 1050 can continue by alerting a user (e.g., a patient, a caregiver, an operator, a physician, etc.) that peritonitis was detected (e.g., at, block 1056). In some embodiments, alerting the user can include providing an alert or notification to the user via an APD machine, in these and other embodiments, the alert can include text or a message (e.g., sent to the user's mobile phone, shown on a display of the APD machine, acid/or otherwise presented to the user), one or more sounds, haptic feedback, and/or any other suitable alert. In at least some embodiments, such as those described above regarding FIGS. 7 and 8, block 1058 may be omitted.

In some embodiments, a patient or user can perform (e.g., manually perform) one or more steps of the method 1050. In at least some embodiments, for example, the patient can align the portion of the disposable set with the peritonitis sensor (block 1052); can capture one or more peritonitis measurements (block 1054) (e.g., by counting the number of dots 315 (as described regarding FIGS. 3A and 3B)), determining the stance of an animal depicted in an optical element (as described regarding FIG. 4), etc.); and/or can determine whether the peritonitis measurement(s) indicate peritonitis (block 1056) (e.g., by comparing the countered number of dots 315 to a known or reference number of dots (as described regarding FIGS. 3A and 3B), by determining whether the stance of the animal is associated with peritonitis, etc.).

Although the steps of method 1050 are discussed and illustrated in a particular order, the method 1050 illustrated in FIG. 10 is not so limited. In other embodiments, method 1050 can be performed in a different order. In these and other embodiments, any of the steps of method 1050 can be performed before, during, and/or after any of the other steps of method 1050. Moreover, a person of ordinary skill in the relevant art will recognize that the illustrated method 1050 can be altered and still remain within these and other embodiments of the present technology. For example, one or more steps of the method 1050 illustrated in FIG. 10 can be omitted and/or repeated in some embodiments.

Although not shown so as to avoid unnecessarily obscuring the description of the embodiments of the technology, any of the devices, systems, and, methods described above can include and/or be performed by a computing device configured to direct and/or arrange components of the systems and/or to receive, arrange, store, analyze, and/or otherwise process data received, for example, from the APD system and/or other components of the APD system (e.g., the peritonitis sensor, etc.). As such, such a computing device includes the necessary hardware and corresponding computer-executable instructions to perform these tasks. More specifically, a computing device configured in accordance with an embodiment of the present technology can include a processor, a storage device, input/output device, one or more sensors, and/or any other suitable subsystems and/or components (e.g., displays, speakers, communication modules, etc.). The storage device can include a set of circuits or a network of storage components configured to retain information and provide access to the retained information. For example, the storage device can include volatile and/or non-volatile memory. As a more specific example, the storage device can include random access memory (RAM), magnetic disks or tapes, and/or flash memory.

The computing device can also include (e.g., non-transitory) computer readable media (e.g., the storage device, disk drives, and/or other storage media) including computer-executable instructions stored thereon that, when executed by the processor and/or computing device, cause the systems to perform one or more of the methods described herein. Moreover, the processor can be configured for performing or otherwise controlling steps, calculations, analysis, and any other functions associated with the methods described herein.

In some embodiments, the storage device can store one or more databases used to store data collected by the systems as well as data used to direct and/or adjust components of the systems. In one embodiment, for example, a database is an HTML file designed by the assignee of the present disclosure. In other embodiments, however, data is stored in other types of databases or data files.

One of ordinary skill in the art will understand that various components of the systems (e.g., the computing device) can be further divided into subcomponents, or that various components and functions of the systems may be combined and integrated. In addition, these components can, communicate via wired and/or wireless communication, as well as information contained in the storage media.

C. Examples

Several aspects of the present technology are set forth in the following examples. Although several aspects of the present technology are set forth in examples specifically directed to systems, methods, and computer-readable mediums; any of these aspects, of the present technology can similarly be set forth in examples directed to any of devices, systems, methods, and computer-readable mediums in other embodiments.

1. An automated peritoneal dialysis (API)) system, comprising:

a disposable set including a drain bag, and a peritonitis sensor configured to capture one or more peritonitis measurements from solution in the disposable set when a portion of the disposable set is at least partially aligned with the peritonitis sensor,

wherein the one or more peritonitis measurements indicate whether peritonitis is likely present within a patient from which the solution is drained.

2. The APD system of example 1, further comprising a detection feature, and wherein:

the detection feature is positioned on or is at least partially aligned with the portion of the disposable set such that the solution is positioned between the detection feature and the peritonitis sensor when the solution is in the portion of the disposable set; and to capture the one or more peritonitis measurements, the peritonitis sensor is configured to obtain one or more images of the detection feature through the solution.

3. The APD system of example 1 or example 2, further comprising a display at least partially aligned with the peritonitis sensor such that the portion of the disposable set is positioned between the display and the peritonitis sensor, wherein the display is configured to display the detection feature.

4. The APD system of example 1 or example 2, wherein:

the drain bag further includes a first side and a second side opposite the first side;

the first side includes the detection feature; and the second side is positioned at least partially between the first side and the peritonitis sensor.

5. The APD system of any of examples 2-4 Wherein the detection feature includes text, an image, indicia, an optical illusion graphic element, or a pattern.

6. The APD system of any of examples 1-5 wherein the peritonitis sensor includes a diagnostic device fluidly coupled to the drain bag.

7. The APD system of example 6 wherein the diagnostic device includes a test strip configured to detect peritonitis when placed in contact with the solution.

8. The APD system of any of examples 1-7, wherein:

the portion of the disposable set further includes a lumen fluidly coupled to the drain bag;

the peritonitis sensor includes (a) a light-detecting element positioned at a first end portion of the lumen and (b) one or more lighting elements positioned at a second end portion of the lumen opposite the first end portion;

the one or more lighting elements are configured to emit light through a center of the lumen and toward the light-detecting element, and the light-detecting element is configured to detect the light from the one or more lighting elements.

The APD system of example 8 wherein:

the one or more lighting elements include a first lighting element and a second lighting element;

the first lighting element is configured to emit first light of a first wavelength toward the light-detecting element; and the second lighting element is configured to emit a second light of a second wavelength toward the light-detecting element.

10. The APD system of example 9 wherein the first wavelength corresponds to red light and the second wavelength corresponds to blue light.

11. The APD system of any of examples 1-7, wherein:

the portion of the disposable set further includes a lumen or cavity fluidly coupled to the drain bag;

the peritonitis sensor includes (a) one or more lighting elements and a light-detecting element positioned on a first side of the lumen or the cavity, and (b) a reflective element positioned (i) at a second side of the lumen or the cavity opposite the first side and (ii) at least partially between the one or lighting elements and the light-detecting element;

the one or more lighting elements are configured to emit light at least partially through the lumen and toward the reflective element; and the light-detecting element is configured to detect portions of the light, reflected from the reflective element.

12. The APD system of example 11 wherein:

the one or more lighting elements include a first lighting element and a second lighting element;

the first lighting element is configured to emit a first light of a first wavelength toward the light-detecting element; and the second lighting element is configured to emit a second light of a second wavelength toward the light-detecting element.

13. The APD system of example 12 wherein the first wavelength corresponds to red light, and the second wavelength corresponds to blue light.

14. A method for detecting peritonitis in a disposable set of an automated peritoneal dialysis (APD) system, the method comprising:

aligning a portion of the disposable set with a peritonitis sensor;

capturing, via the peritonitis sensor, one or more peritonitis measurements from solution in the disposable set; and determining if the one or more peritonitis measurements indicate a presence of peritonitis in a patient from which the solution was drained.

15. The method of example 14, further comprising alerting a user of the APD system that the one or more peritonitis measurements indicate the presence of peritonitis.

16. The method of example 14 or example 15 wherein aligning the portion of the disposable set with the peritonitis sensor includes aligning a detection feature of the disposable set with an imaging component of the peritonitis sensor.

17. The method of example 13 wherein capturing one or more peritonitis measurements includes capturing, via the imaging component, one or more images of the detection feature.

18. The method of any one of examples 14-17 wherein determining that the one or more peritonitis measurements indicate the presence of peritonitis includes:

comparing (a) one or more images of a detection feature positioned on or aligned with the portion of the disposable set with (b) one or more reference images;

using optical character recognition (OCR) to determine a reading of the text in the one or more images and comparing the reading to reference text; or using OCR to determine a count of one or more elements of a pattern in the one or more images and comparing the count to a reference count.

19. The method of example 18 wherein determining that the one or more peritonitis measurements indicate the presence of peritonitis includes:

determining that the one or more images of the detection feature vary from the one or more reference images by more than a first threshold amount;

determining that the reading of the text differs from the reference text by more than a second threshold amount; or determining that the count differs from the reference count by inure than a third threshold amount.

20. The method of example 14 or example 15 wherein:
the portion of the disposable set includes a portion of a
    fluid line; and
aligning the portion of the disposable set with the peri-
    tonitis sensor includes aligning the portion of the fluid
    line between (a) a light-detecting element and (b) one
    or more lighting elements configured to emit light
    toward the light-detecting element, such that the light
    propagates (i) in a direction parallel to the portion of the
    fluid line and (ii) within an interior of the portions of
    the fluid line.

21. The method of example 14 or example 15 wherein:
the portion of the disposable set includes a portion of a
    fluid line having a reflective element; and
aligning the portion of the disposable set with the peri-
    tonitis sensor includes aligning the portion of the
    reflective element with (a) a light-detecting element
    and (h) one or more lighting elements configured to
    emit light toward the reflective element, such that the
    light propagates (i) in a first direction toward the
    reflective element and (ii) in a second direction toward
    the light-detecting element at least partially within an
    interior of Me portion of the fluid line.

22. The method of example 20 or example 21 wherein
capturing one or more peritonitis measurements includes
detecting, via the light-detecting elements, an amount of the
light from the one or more lighting elements.

23. The method of example 22 wherein determining that
the one or more peritonitis measurements indicate the pres-
ence of peritonitis includes comparing the detected amount
With one or more reference amounts.

24. The method of example 14 or example 15 wherein:
the peritonitis sensor includes a diagnostic device having
    a test strip; and
aligning the portion of the disposable set with the peri-
    tonitis sensor includes placing the test strip in direct
    contact with the solution.

25. The method of example 24 wherein capturing the one
or more peritonitis measurements includes performing, via
the test strip, one or more chemical reactions to detect
peritonitis.

26. The method of example 25 wherein determining that
the one or more peritonitis measurements indicate the pres-
ence of peritonitis includes reading an indicator of the test
strip to determine results of the one or more chemical
reactions.

27. A non-transitory, computer-readable medium having
instructions stored thereon that, when executed by one or
more processors of an automated peritoneal dialysis (APD)
system, cause the APD system to perform a method com-
prising:
    capturing, via a peritonitis sensor of the APD system, one
        or more peritonitis measurements from solution in a
        disposable set of the APD system; and
    determining whether the one or more peritonitis measure-
        ments indicate a presence of peritonitis in a patient
        from which the solution is drained.

28. The computer-readable medium of example 27
wherein capturing the one or more peritonitis measurements
includes:
    capturing, via the peritonitis sensor, one or more images
        of a detection feature positioned on or aligned with a
        first portion of the disposable set; or
    detecting, via a light-detecting element of the APD sys-
        tem, an amount of light from one or more lighting
        elements of the APD system and emitted along a
        second portion of the disposable set.

29. The computer-readable medium of example 27 or
example 28 wherein determining whether the one or More
peritonitis measurements indicate the presence of peritonitis
includes:
    comparing (a) one or more images of a detection feature
        positioned on or aligned with a portion of the dispos-
        able set with (b) one or more reference images of the
        detection feature;
    using optical character recognition (OCR) to determine a
        reading of text in the one or more images of the
        detection feature and comparing the reading to refer-
        ence text;
    using OCR to determine a count of one or more elements
        of a pattern in the one or more images of the detection
        feature and comparing the count to a reference number
        of the one or more elements; or
    comparing one or more amounts of light detected by a
        light-detecting element with one or more reference
        amounts.

30. The computer-readable medium of example 29
wherein determining whether the one or more peritonitis
measurements indicate the presence of peritonitis includes:
    determining that the one or more images of the detection
        feature vary from the one or more reference images of
        the detection feature by more than a first threshold
        amount;
    determining that the reading of the text differs from the
        reference text by more than a second threshold amount;
    determining that the count differs from the reference
        number by more than a third threshold amount; or
    determining, that the one or more amounts of light are
        below the one or more reference amounts.

D. Conclusion

From the foregoing, it will be appreciated that specific
embodiments of the technology have been described herein
for purposes of illustration, but well-known structures and
functions have not been shown or described in detail to
avoid unnecessarily obscuring the description of the
embodiments of the technology. To the extent, any materials
incorporated herein by reference conflict with the present
disclosure, the present disclosure controls. Where the con-
text permits, singular or plural terms can also include the
plural or singular term, respectively. Moreover, unless the
word "or" is expressly limited to mean only a single item
exclusive from the other items in reference to a list of two
or more items, then the use of "or" in such a list is to be
interpreted as including (a) any single item in the list, (b) all
of the items in the list, or (c) any combination of the items
in the list. As used herein, the phrase "and/or" as in "A
and/or B" refers to A alone, B alone, and both A and B.
Where the context permits, singular or plural terms can also
include the plural or singular term, respectively. Addition-
ally, the terms "comprising," "including," "having" and
"with" are used throughout to mean including at least the
recited feature(s) such that any greater number of the same
feature and/or additional types of other features are not
precluded.

Furthermore, as used herein, the term "substantially"
refers to the complete or nearly complete extent or degree of
an action, characteristic, property, state, structure, item, or
result. For example, an object that is "substantially"
enclosed would mean that the object is either completely
enclosed or nearly completely enclosed. The exact allowable
degree of deviation from absolute completeness may in
some cases depend on the specific context. However, generally speaking, the nearness of completion will be so as to have the same overall result as if absolute and total completion were obtained. The use of "substantially" is equally applicable when used in a negative connotation to refer to the complete or near complete lack of an action, characteristic, property, state, structure, item, or result. Moreover, the terms "connect" and "couple" are used interchangeably herein and refer to both direct and indirect connections or couplings. For example, where the context permits, element A "connected" or "coupled" to element B can refer (i) to A directly "connected" or directly "coupled" to B and/or (ii) to A indirectly "connected" or indirectly "coupled" to B.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant an will recognize. For example, while steps are presented in a given order, alternative embodiments can perform steps in a different order. As another example, various components of the technology can be further divided into subcomponents, and/or various components and/or functions of the technology can be combined and/or integrated. Furthermore, although advantages associated with certain embodiments of the technology have been described in the context of those embodiments, other embodiments can also exhibit such advantages, and not all embodiments need necessarily exhibit such advantages to fall within the scope of the technology.

It should also be noted that other embodiments in addition to those disclosed herein are within the scope of the present technology. For example, embodiments of the present technology can have different configurations, components, and/ or procedures in addition to those shown or described herein. Moreover, a person of ordinary skill in the art will understand that these and other embodiments can be without several of the configurations, components, and/or procedures shown or described herein without deviating from the present technology. Accordingly, the disclosure and associated technology can encompass other embodiments not expressly shown or described herein.

We claim:

1. An automated peritoneal dialysis (APD) system, comprising:

a disposable set including a drain bag; and a peritonitis sensor configured to capture one or more peritonitis measurements from a solution in the disposable set when a portion of the disposable set is at least partially aligned with the peritonitis sensor, wherein the one or more peritonitis measurements indicate whether peritonitis is present within a patient from which the solution is drained, wherein the APD system is configured to determine that the one or more peritonitis measurements indicate peritonitis by:

using optical character recognition (OCR) to determine a reading of text in one or more images and comparing the reading to reference text; or using OCR to determine a count of one or more elements of a pattern in the one or more images and comparing the count to a reference count.

2. The APD system of claim 1, further comprising a detection feature, and wherein:

the detection feature is configured to be positioned on or at least partially aligned with the portion of the disposable set such that the solution is positioned between the detection feature and the peritonitis sensor when the solution is in the portion of the disposable set; and to capture the one or more peritonitis measurements, the peritonitis sensor is configured to obtain the one or more images of the detection feature through the solution.

3. The APD system of claim 2, further comprising a display at least partially aligned with the peritonitis sensor such that the portion of the disposable set is positioned between the display and the peritonitis sensor, wherein the display is configured to display the detection feature.

4. The APD system claim 2, wherein:

the drain bag further includes a first side and a second side opposite the first side;

the first side includes the detection feature; and the second side is positioned at least partially between the first side and the peritonitis sensor.

5. The APD system of claim 2 wherein the detection feature includes text, an image, indicia, an optical illusion graphic element, or a pattern.

6. The APD system of claim 1, wherein the APD system is configured to determine that the one or more peritonitis measurements indicate peritonitis by using optical character recognition (OCR) to determine the reading of the text in the one or more images and comparing the reading to the reference text.

7. The APD system of claim 1, wherein the APD system is configured to determine that the one or more peritonitis measurements indicate peritonitis by using OCR to determine the count of the one or more elements of the pattern in the one or more images and comparing the count to the reference count.

8. The APD system of claim 1, wherein the APD system is configured to alert a user of the APD system that the one or more peritonitis measurements indicate peritonitis.

9. The APD system of claim 1, wherein the APD system is configured to capture, via an imaging component, one or more images of a detection feature.

10. A method for detecting peritonitis in a disposable set of an automated peritoneal dialysis (APD) system, the method comprising:

aligning a portion of the disposable set with a peritonitis sensor;

capturing, via the peritonitis sensor, one or more peritonitis measurements from a solution in the disposable set; and determining that the one or more peritonitis measurements indicate a presence of peritonitis in a patient from which the solution was drained, wherein determining that the one or more peritonitis measurements indicate the presence of peritonitis comprises:

using optical character recognition (OCR) to determine a reading of text in the one or more images and comparing the reading to reference text; or using OCR to determine a count of one or more elements of a pattern in the one or more images and comparing the count to a reference count.

11. The method of claim 10, wherein determining that the one or more peritonitis measurements indicate the presence of peritonitis includes:

determining that the reading of the text differs from the reference text by more than a first threshold amount; or determining that the count differs from the reference count by more than a third second threshold amount.

12. The method of claim 10, wherein determining that the one or more peritonitis measurements indicate the presence of peritonitis comprises using optical character recognition (OCR) to determine the reading of the text in the one or more images and comparing the reading to the reference text.

13. The method of claim 10, wherein determining that the one or more peritonitis measurements indicate the presence of peritonitis comprises using OCR to determine the count of the one or more elements of the pattern in the one or more images and comparing the count to the reference count.

14. The method of claim 10, further comprising alerting a user of the APD system that the one or more peritonitis measurements indicate the presence of peritonitis.

15. The method of claim 10, wherein aligning the portion of the disposable set with the peritonitis sensor includes aligning a detection feature of the disposable set with an imaging component of the peritonitis sensor.

16. The method of claim 15, wherein capturing one or more peritonitis measurements includes capturing, via the imaging component, one or more images of the detection feature.

17. The method of claim 10, wherein:

a drain bag of the disposable set includes a first side and a second side opposite the first side;

the first side includes a detection feature; and the second side is positioned at least partially between the first side and the peritonitis sensor.

18. A non-transitory computer-readable medium having instructions stored thereon that, when executed by one or more processors of an automated peritoneal dialysis (APD) system, cause the APD system to perform functions comprising:

capturing, via a peritonitis sensor, one or more peritonitis measurements from a solution in a disposable set; and determining that the one or more peritonitis measurements indicate a presence of peritonitis in a patient from which the solution was drained, wherein determining that the one or more peritonitis measurements indicate the presence of peritonitis comprises:

using optical character recognition (OCR) to determine a reading of text in the one or more images and comparing the reading to reference text; or using OCR to determine a count of one or more elements of a pattern in the one or more images and comparing the count to a reference count.

19. The non-transitory computer-readable medium of claim 18, wherein determining that the one or more peritonitis measurements indicate the presence of peritonitis comprises determining that the reading of the text differs from the reference text by more than a threshold amount.

20. The non-transitory computer-readable medium of claim 18, wherein determining that the one or more peritonitis measurements indicate the presence of peritonitis comprises determining that the count differs from the reference count by more than a threshold amount.

* * * * *